US005888736A

United States Patent [19]
Lacroix et al.

[11] Patent Number: 5,888,736
[45] Date of Patent: *Mar. 30, 1999

[54] METHOD, COMPOSITIONS AND KIT FOR DETECTION AND IDENTIFICATION OF MICROORGANISMS

[75] Inventors: Jean-Michel Lacroix, Etobicoke; James Leushner, North York; May Hui, Toronto; James M. Dunn, Scarborough, all of Canada; Marina T. Larson, Yorktown, N.Y.

[73] Assignee: Visible Genetics, Inc., Toronto, Canada

[*] Notice: The term of this patent shall not extend beyond the expiration date of Pat. No. 5,830,657.

[21] Appl. No.: 807,138

[22] Filed: Feb. 27, 1997

Related U.S. Application Data

[63] Continuation-in-part of Ser. No. 684,498, Jul. 19, 1996, Pat. No. 5,830,657, Ser. No. 640,672, May 1, 1996, Pat. No. 5,789,168, and Ser. No. 577,858, Dec. 22, 1995, Pat. No. 5,834,189.

[51] Int. Cl.$^6$ ............................... C12Q 1/68; C12P 19/34
[52] U.S. Cl. ............................................. 435/6; 435/91.2
[58] Field of Search ........................ 435/6, 91.2; 436/94, 436/800; 536/24.32, 24.33; 935/77, 78

[56] References Cited

U.S. PATENT DOCUMENTS

| | | | |
|---|---|---|---|
| 4,683,194 | 7/1987 | Saiki et al. | 435/6 |
| 4,683,195 | 7/1987 | Mullis et al. | 435/6 |
| 4,683,202 | 7/1987 | Mullis | 435/91 |
| 4,729,947 | 3/1988 | Middendorf et al. | 435/6 |
| 4,795,699 | 1/1989 | Tabor et al. | 435/5 |
| 4,800,159 | 1/1989 | Mullis et al. | 435/172.3 |
| 4,811,218 | 3/1989 | Hunkapiller et al. | 364/413.01 |
| 4,889,818 | 12/1989 | Gelfand et al. | 435/194 |
| 4,942,124 | 7/1990 | Church | 435/6 |
| 4,965,188 | 10/1990 | Mullis et al. | 435/6 |
| 5,008,182 | 4/1991 | Sninsky et al. | 435/5 |
| 5,075,216 | 12/1991 | Innis et al. | 435/6 |
| 5,079,352 | 1/1992 | Gelfand et al. | 538/27 |
| 5,122,345 | 6/1992 | Tabor et al. | 422/116 |
| 5,124,247 | 6/1992 | Ansorge | 435/6 |
| 5,171,534 | 12/1992 | Smith et al. | 422/82.05 |
| 5,175,082 | 12/1992 | Jeffreys | 435/6 |
| 5,176,995 | 1/1993 | Sninsky et al. | 435/6 |
| 5,207,880 | 5/1993 | Middendorf et al. | 204/182.8 |
| 5,283,171 | 2/1994 | Manos et al. | 435/5 |
| 5,352,600 | 10/1994 | Gelfand et al. | 435/194 |
| 5,427,911 | 6/1995 | Ruano | 435/6 |
| 5,453,355 | 9/1995 | Birkenmeyer et al. | 435/6 |
| 5,527,898 | 6/1996 | Bauer et al. | 536/24.3 |
| 5,830,657 | 11/1998 | Leushner et al. | 435/6 |

FOREIGN PATENT DOCUMENTS

| | | |
|---|---|---|
| 0265293 | 4/1988 | European Pat. Off. |
| 0386859 | 9/1990 | European Pat. Off. |
| 0655506 | 5/1995 | European Pat. Off. |
| 8907149 | 8/1989 | WIPO . |
| 9218650 | 10/1992 | WIPO . |
| 9302212 | 2/1993 | WIPO . |
| 9308305 | 4/1993 | WIPO . |
| 9426894 | 11/1994 | WIPO . |
| 95/04140 | 2/1995 | WIPO . |
| 9506756 | 3/1995 | WIPO . |
| 9601909 | 1/1996 | WIPO . |

OTHER PUBLICATIONS

Rao, V. B., "Direct–Sequencing of Polymerase Chain Reaction–Amplified DNA", *Anal Biochem,* 216: 1–14 (1994).

Kretz et al., "Cycle Sequencing" in *PCR Methods and Applications* 3: S107–S112 (1994).

Deng et al., "Simultaneous amplification and sequencing of genomic DNA (SAS): sequencing of 16S rRNA genes using total genomic DNA from *Butyrovibrio fibrisolvens,* and detection and genotyping of non–cultruable mycoplasma–like organisms directly from total DNA isolated from infected plants", *J. Microbiol. Methods* 17: 103–113 (1993).

Gyllenstein et al., "Generation of single–stranded DNA by polymerase chain reaction and its application to direct sequencing of the HLA–DQA locus", *Proc. Nat'l Acad. Sci. USA* 85: 7652–7656 (1988).

Mullis et al., "Specific Synthesis of DNA in Vitro via a Polymerase–Catalyzed Chain Reaction" *Meth. Enzymol.* 155: 335–350 (1987).

Ruano et al., "Genotyping and haplotyping of polymorphisms directly from genomic DNA via coupled amplification and sequencing (CAS)" *Nucl. Acids Res.* 19: 6877–6882 (1991).

Miller et al., "Chain Terminator Sequencing of Double–Stranded DNA With Built in Error Correction", General Atomics Pre–Print (1991).

Nuovo, G.J., "In situ PCR" in Dieffenbach et al., *PCR Primer: A Laboratory Manual,* pp. 235–248, Cold Spring Harbor Laboratory Press (1995).

Roemer et al., "Simultaneous Bi–Directional Cycle Sequencing", Poster presented at 9$^{th}$ International Genome Sequencing and Analysis Conference, Hilton Head, SC, Sep. 1997.

Tabor et al., "A single residue in DNA Polymerases of the *Escherichia coli* DNA polymerase I family is critical for distinguishing between deoxy and dideoxynucleotides", *Proc. Nat'l Acad. Sci. USA.* 92: 6339–6343 (1995).

Reeve et al., A novel thermostable polymerase for DNA sequencing *Nature* 376: 796–797 (1995).

(List continued on next page.)

*Primary Examiner*—George C. Elliott
*Assistant Examiner*—Thomas G Larson
*Attorney, Agent, or Firm*—Oppedahl & Larson LLP

[57] ABSTRACT

Evaluation of a sample for the presence and qualitative nature of a microorganism can be performed in a single vessel by combining a natural abundance DNA sample with a sequencing mixture containing a primer pair, a thermally stable polymerase such as ThermoSequenase™ which incorporates dideoxynucleotides into an extending nucleic acid polymer at a rate which is no less than about 0.4 times the rate of incorporation of deoxynucleotides, nucleotide triphosphate feedstocks, and a chain terminating nucleotide triphosphate. The mixture is processed through multiple thermal cycles for annealing, extension and denaturation to produce a product mixture which is analyzed by electrophoresis.

11 Claims, No Drawings

OTHER PUBLICATIONS

Sarkar et al., "Dideoxy Fingerprinting (ddF): A rapid and Efficient Screen for the Presence of Mutations" *Genomics* 13: 441–443 (1992).

Wiemann et al., "Simultaneous On–Line Sequencing on Both Strands with Two Fluorescent Dyes" *Anal. Biochem.* 224: 117–121 (1995).

Murakawa et al., :Direct Detection of HIV–1 RNA from AIDS and ARC Patient Samples *DNA* 7: 287–295 (1988).

Carothers et al., "Point Mutation Analysis in A Mammalian Gene: Rapid Preparation of Total RNA, PCR Amplification of cDNA, and Tag Sequencing by a Novel Method" *BioTechniques* 7: 494–498 (1989).

Murray, V., "Improved Double–Stranded DNA Sequencing Using the Linear Polymerase Chain Reaction", *Nucl. Acids Res.* 17: 8889 (1989).

Mahony et al., "Multiplex PCR for Detection of *Chlamydia trachomatis* and *Neisseria gonorhoeae* in Genitourinary specimens" *J. Clin. Microbiol.* 33: 3049–3053 (1995).

Kaltenboeck et al, "Two–Step Polymerase Chain Reaction and Restriction Endonuclease Analyses Detect and Differentiate ompA DNA of Chlmaydia spp." *J. Clin. Microbiol.* 30: 1098–1104 (1992).

Mahony et al., "Confirmatory Polymerase Chain Reaction Testing for *Chlamydia trachomatis* in First–Void Urine from Asymptomatic and Symptomatic Men" *J. Clin. Microbiol.* 30: 2241–2245 (1992).

Ruano et al., "Coupled Amplification and sequencing of geneomic DNA", *Proc. Nat'l Acad. Sci (USA)* 88: 2815–2819 (1991).

Ewanowitch et al., "Major Outbreak of Pertussis in Northern Alberta Canada: Analysis of Discrepant Direct Fluorescent–Antibody Culture Results by Using Polymerase Chain Reaction Methodology" *J. Clin. Microbiol.* 31: 1715–1725 (1993).

Erickson, D., "Diagnosis by DNA", *Scientific American*, p. 116 (1992).

Eisenstein, B., "The Polymerase Chain Reaction", *New Engl. J., Med.* 332: 178–183 (1990).

De Schryver et al., "Epidemiology of sexually transmitted diseases: the global picture", *Bull. WHO* 68: 639–654 (1990).

Church et al., "The Genomic Sequencing Technique", *Medical Genetics: Past, Present, Future* pp. 17–21 (1985).

Church et al., "Genomic Sequencing", *Proc. Nat'l Acad. Sci. (USA)* 81: 1991–1995 (1984).

Bej et al., "Multiplex PCR amplification and immobilized cap[utre probes for detection of bacterial pathogens and indicators in water" *Molec. Cellular Probes* 4: 353–365 (1990).

Bej et al., "Detection of Coliform Bacteria and *Escherichia coli* by Multiplex Chain Reaction: Comparison with Defined Substrate and Plating Methods for Water Quality Monitoring" *Appl. Environ. Microbiol.* 57: 2429–2432 (1991).

Beebe et al., "Incidence of *Neisseria gonorrhoeae* Isolates Negative by Syva DDirect Fluorescent–Antibody Test but Positve by Gen–Prove Accuprobe Test in a Sexually Transmitted Disease Clinic Population" *J. Clim. Microbiol.* 31: 2535–2537 (1993).

Way et al., "Specific Detection of Salmonella spp. by Multiplex Polymerase Chain Reaction" *Appl. Environ. Microbiol.* 59: 1473–1479 (1993).

Warren et al., "Comparative Evaulation of Detection Assays for *Chlamydia trachomatis*" *J. Clin. Microbiol.* 31: 1663–1666 (1993).

Thermosequenase Product Insert (1995).

Maxam et al., "A new method for sequencing DNA", *Proc. Nat'l. Acad. Sci. (USA)* 74: 560–564 (1977).

Smith et al., "Fluorescence Detection in automated DNA Sequence analysis" *Nature* 321: 674–679 (1986).

Langemeier et al., "Application of Cycle Dideoxy Fingerprinting to Screening Heterogeneous Polpulations of the Equine Infectious Anemia Virus", *Biotechniques* 17 (1994).

Ruano et al., Automated Genomic Coupled Amplification and Sequencing (CAS) of the Mitochondrial D Loop, Genomic Analysis Conference, Hilton Head, Fall 1994.

Arnot et al. "Digital codes from hypervariable tandemly repeated DNA sequences in the *Plasmodium falciparum* circumsporozoite gene can genetically barcode isolates" *Molec. Biochem. Parasitol.* 61: 15–24 (1993).

Ellison et al., "Detection of Mutations and Polymorphisms Using Fluorescence–Based Dideoxy Fingerprinting (F–ddF)", *Biotechniques* 17: 742–753 (1994).

Sanger et al., "DNA sequencing with chain–terminating inhibitors" *Proc. Nat'l. Acad. Sci.* 74: 5463–5467 (1977).

SEQUENCE LISTING ( 1 ) GENERAL INFORMATION:

( i i i ) NUMBER OF SEQUENCES: 189

( 2 ) INFORMATION FOR SEQ ID NO: 1:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
        ( A ) ORGANISM: Chlamydia trachomatis ( x i ) FEATURE:
        ( D ) OTHER INFORMATION: primer for sequencing of cryptic
            plasmis ( x i ) SEQUENCE DESCRIPTION: SEQ ID NO:1:

TCCGGAGCGA GTTACGAAGA 20

( 2 ) INFORMATION FOR SEQ ID NO: 2:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: Chlamydia trachomatis ( i x ) FEATURE:
        ( D ) OTHER INFORMATION: primer for sequencing of cryptic
            plasmid ( x i ) SEQUENCE DESCRIPTION: SEQ ID NO:2:

ATTCAATGCC CGGGATTGGT 20

( 2 ) INFORMATION FOR SEQ ID NO: 3:

( i ) SEQUENCE CHARACTERISTICS:
    ( A ) LENGTH: 25
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
    ( A ) ORGANISM: Chlamydia trachomatis ( i x ) FEATURE:
    ( D ) OTHER INFORMATION: primer for sequencing of VS regions ( x i ) SEQUENCE DESCRIPTION: SEQ ID NO:3:

CCGACCGCGT CTTGAAAACA GATGT     25

( 2 ) INFORMATION FOR SEQ ID NO: 4:

( i ) SEQUENCE CHARACTERISTICS:
    ( A ) LENGTH: 21
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
    ( A ) ORGANISM: Chlamydia trachomatis ( i x ) FEATURE:
    ( D ) OTHER INFORMATION: primer for sequencing of VS regions ( x i ) SEQUENCE DESCRIPTION: SEQ ID NO:4:

CACCCACATT CCCAGAGAGC T     21

( 2 ) INFORMATION FOR SEQ ID NO: 5:

( i ) SEQUENCE CHARACTERISTICS:
    ( A ) LENGTH: 21
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
    ( A ) ORGANISM: Chlamydia trachomatis ( i x ) FEATURE:
    ( D ) OTHER INFORMATION: primer for sequencing of VS regions ( x i ) SEQUENCE DESCRIPTION: SEQ ID NO:5:

CGTGCAGCTT TGTGGGAATG T     21

( 2 ) INFORMATION FOR SEQ ID NO: 6:

( i ) SEQUENCE CHARACTERISTICS:
  ( A ) LENGTH: 24
  ( B ) TYPE: nucleic acid
  ( C ) STRANDEDNESS: double
  ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
  ( A ) ORGANISM: Chlamydia trachomatis ( i x ) FEATURE:
  ( D ) OTHER INFORMATION: primer for sequencing of VS regions ( x i ) SEQUENCE DESCRIPTION: SEQ ID NO:6:

CTAGATTTCA TCTTGTTCAA TTGC  24

( 2 ) INFORMATION FOR SEQ ID NO: 7:

( i ) SEQUENCE CHARACTERISTICS:
  ( A ) LENGTH: 23
  ( B ) TYPE: nucleic acid
  ( C ) STRANDEDNESS: double
  ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
  ( A ) ORGANISM: Chlamydia trachomatis ( i x ) FEATURE:
  ( D ) OTHER INFORMATION: primer for sequencing of VS regions ( x i ) SEQUENCE DESCRIPTION: SEQ ID NO:7:

AGCATGCGTR TKGGTTACTA YGG  23

( 2 ) INFORMATION FOR SEQ ID NO: 8:

( i ) SEQUENCE CHARACTERISTICS:
  ( A ) LENGTH: 24
  ( B ) TYPE: nucleic acid
  ( C ) STRANDEDNESS: double
  ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
  ( A ) ORGANISM: Chlamydia trachomatis ( i x ) FEATURE:
  ( D ) OTHER INFORMATION: primer for sequencing of VS regions ( x i ) SEQUENCE DESCRIPTION: SEQ ID NO:8:

TGACTTTGTT TTCGACCGYG TTTT  24

( 2 ) INFORMATION FOR SEQ ID NO: 9:

( i ) SEQUENCE CHARACTERISTICS:
        ( A ) LENGTH: 23
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: Chlamydia trachomatis ( i x ) FEATURE:
        ( D ) OTHER INFORMATION: primer for sequencing of VS regions ( x i ) SEQUENCE DESCRIPTION: SEQ ID NO:9:

CTAAAGTYGC RCATCCACAT TCC        23

( 2 ) INFORMATION FOR SEQ ID NO: 10:

( i ) SEQUENCE CHARACTERISTICS:
        ( A ) LENGTH: 23
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: Chlamydia trachomatis ( i x ) FEATURE:
        ( D ) OTHER INFORMATION: primer for sequencing of VS regions ( x i ) SEQUENCE DESCRIPTION: SEQ ID NO:10:

CATCCACATT CCCASARAGC TGC        23

( 2 ) INFORMATION FOR SEQ ID NO: 11:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: Chlamydia trachomatis ( i x ) FEATURE:
        ( D ) OTHER INFORMATION: primer for sequencing of cryptic
            plasmid ( x i ) SEQUENCE DESCRIPTION: SEQ ID NO:11:

ATGCCCGGGA TTGGTTGATC        20

( 2 ) INFORMATION FOR SEQ ID NO: 12:

( i ) SEQUENCE CHARACTERISTICS:
            ( A ) LENGTH: 20
            ( B ) TYPE: nucleic acid
            ( C ) STRANDEDNESS: double
            ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
            ( A ) ORGANISM: Chlamydia trachomatis ( i x ) FEATURE:
            ( D ) OTHER INFORMATION: primer for sequencing of VS regions ( x i ) SEQUENCE DESCRIPTION: SEQ ID NO:12:

GGAGACTTTG TTTTCGACCG                                                20

( 2 ) INFORMATION FOR SEQ ID NO: 13:

( i ) SEQUENCE CHARACTERISTICS:
            ( A ) LENGTH: 20
            ( B ) TYPE: nucleic acid
            ( C ) STRANDEDNESS: double
            ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
            ( A ) ORGANISM: Chlamydia trachomatis ( i x ) FEATURE:
            ( D ) OTHER INFORMATION: primer for sequencing of VS regions ( x i ) SEQUENCE DESCRIPTION: SEQ ID NO:13:

CATTCCCACA AAGCTGCGCG                                                20

( 2 ) INFORMATION FOR SEQ ID NO: 14:

( i ) SEQUENCE CHARACTERISTICS:
            ( A ) LENGTH: 20
            ( B ) TYPE: nucleic acid
            ( C ) STRANDEDNESS: double
            ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
            ( A ) ORGANISM: Chlamydia trachomatis ( i x ) FEATURE:
            ( D ) OTHER INFORMATION: primer for sequencing of VS regions ( x i ) SEQUENCE DESCRIPTION: SEQ ID NO:14:

TTCCCACAAA GCTGCGCGAG                                                                                       20

(2) INFORMATION FOR SEQ ID NO: 15:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: Chlamydia trachomatis (ix) FEATURE:
        (D) OTHER INFORMATION: primer for sequencing of VS regions (xi) SEQUENCE DESCRIPTION: SEQ ID NO:15:

CCCACAAAGC TGCGCGAGCG                                                                                       20

(2) INFORMATION FOR SEQ ID NO: 16:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: Chlamydia trachomatis (ix) FEATURE:
        (D) OTHER INFORMATION: primer for sequencing of ribosomal DNA (xi) SEQUENCE DESCRIPTION: SEQ ID NO: 16:

ACCTTTCGGT TGAGGGAGAG TCTA                                                                                  24

(2) INFORMATION FOR SEQ ID NO: 17:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: Chlamydia trachomatis (ix) FEATURE:
        (D) OTHER INFORMATION: primer for sequencing of ribosomal DNA (xi) SEQUENCE DESCRIPTION: SEQ ID NO:17:

GGACCAATTC TTATTCCCAA GCGA 24

(2) INFORMATION FOR SEQ ID NO: 18:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: HIV-1

(ix) FEATURE:
        (D) OTHER INFORMATION: primer for sequencing of HIV-1 protease gene (xi) SEQUENCE DESCRIPTION: SEQ ID NO:18:

ATCACTCTTT GGCAACGACC 20

(2) INFORMATION FOR SEQ ID NO: 19:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: HIV-1

(ix) FEATURE:
        (D) OTHER INFORMATION: primer for sequencing of HIV-1 protease gene (xi) SEQUENCE DESCRIPTION: SEQ ID NO:19:

CAGGAGCAGA TGATACAGTA TTAG 24

(2) INFORMATION FOR SEQ ID NO: 20:

(i) SEQUENCE CHARACTERISTICS:
        (A) LENGTH: 25
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: HIV-1

(ix) FEATURE:

(D) OTHER INFORMATION: primer for sequencing of HIV-1 protease gene (xi) SEQUENCE DESCRIPTION: SEQ ID NO:20:

CCATTCCTGG CTTTAATTTT ACTGG 25

(2) INFORMATION FOR SEQ ID NO: 21:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: Human Papillomavirus (ix) FEATURE:
        (D) OTHER INFORMATION: primer for sequencing of HPV (xi) SEQUENCE DESCRIPTION: SEQ ID NO:21:

GCMCAGGGWC ATAAYAATGG 20

(2) INFORMATION FOR SEQ ID NO: 22:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: Human Papillomavirus (ix) FEATURE:
        (D) OTHER INFORMATION: primer for sequencing of HPV (xi) SEQUENCE DESCRIPTION: SEQ ID NO:22:

CGTCCMAARG GAWACTGATC 20

(2) INFORMATION FOR SEQ ID NO: 23:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:23:

TCAAAKGAAT TGACGGGGGC 20

(2) INFORMATION FOR SEQ ID NO: 24:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:24:

AGGCCCGGGA ACGTATTCAC 20

(2) INFORMATION FOR SEQ ID NO: 25:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:25:

TGCCAGCAGC CGCGGTAA 18

(2) INFORMATION FOR SEQ ID NO: 26:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:26:

GGACTACCAG GGTATCTAAT 20

(2) INFORMATION FOR SEQ ID NO: 27:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes ( v ) FRAGMENT TYPE: internal ( x i ) SEQUENCE DESCRIPTION: SEQ ID NO:27:

GAGGAAGGTG GGGATGACGT                                                                                           20

( 2 ) INFORMATION FOR SEQ ID NO: 28:

( i ) SEQUENCE CHARACTERISTICS:
                ( A ) LENGTH: 20
                ( B ) TYPE: nucleic acid
                ( C ) STRANDEDNESS: double
                ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:28:

AGGCCCGGGA ACGTATTCAC                                                                                           20

( 2 ) INFORMATION FOR SEQ ID NO: 29:

( i ) SEQUENCE CHARACTERISTICS:
                ( A ) LENGTH: 21
                ( B ) TYPE: nucleic acid
                ( C ) STRANDEDNESS: double
                ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:29:

GAGAGTTTGA TCCTGGCTCA G                                                                                         21

( 2 ) INFORMATION FOR SEQ ID NO: 30:

( i ) SEQUENCE CHARACTERISTICS:
                ( A ) LENGTH: 20
                ( B ) TYPE: nucleic acid
                ( C ) STRANDEDNESS: double
                ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:30:

CCCACTGCTG CCTCCCGTAG                                                                                           20

( 2 ) INFORMATION FOR SEQ ID NO: 31:

( i ) SEQUENCE CHARACTERISTICS:
                ( A ) LENGTH: 21
                ( B ) TYPE: nucleic acid
                ( C ) STRANDEDNESS: double
                ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:31:

GAGAGTTTGA TCCTGGCTCA G    21

( 2 ) INFORMATION FOR SEQ ID NO: 32:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:32:

TTTCACGAAC AACGCGACAA    20

( 2 ) INFORMATION FOR SEQ ID NO: 33:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:33:

CTCGTCCAGC GCCGCTTCGG    20

( 2 ) INFORMATION FOR SEQ ID NO: 34:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:34:

CCTGCGAGCG TAGGCGTCGG    20

( 2 ) INFORMATION FOR SEQ ID NO: 35:

( i ) SEQUENCE CHARACTERISTICS:
        ( A ) LENGTH: 18
        ( B ) TYPE: nucleic acid
        ( C ) STRANDEDNESS: double (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:35:

TTCTCAATTC GGTAAGGC 18

(2) INFORMATION FOR SEQ ID NO: 36:

(i) SEQUENCE CHARACTERISTICS:
(A) LENGTH: 20
(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:36:

ATATTGACCA GTGCTATTTC 20

(2) INFORMATION FOR SEQ ID NO: 37:

(i) SEQUENCE CHARACTERISTICS:
(A) LENGTH: 29
(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:37:

CAATTGCTTA TAACCTTTTG GTTATAAAT 29

(2) INFORMATION FOR SEQ ID NO: 38:

(i) SEQUENCE CHARACTERISTICS:
(A) LENGTH: 27
(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:38:

TATAGGTACC GTCATTATCT TCCCTAT 27

(2) INFORMATION FOR SEQ ID NO: 39:

(i) SEQUENCE CHARACTERISTICS:
(A) LENGTH: 25
(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:39:

TTATGAAAAA ATATTTATTG GGAAT 25

(2) INFORMATION FOR SEQ ID NO: 40:

(i) SEQUENCE CHARACTERISTICS:
(A) LENGTH: 25
(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:40:

CTTTAAGCTC AAGCTTGTCT ACTGT 25

(2) INFORMATION FOR SEQ ID NO: 41:

(i) SEQUENCE CHARACTERISTICS:
(A) LENGTH: 25
(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:41:

CTGCAGCTTG GAATTCAGGC ACTTC 25

(2) INFORMATION FOR SEQ ID NO: 42:

(i) SEQUENCE CHARACTERISTICS:
(A) LENGTH: 24
(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:42:

GTTTTGTAAT TTCAACTGCT GACC 24

( 2 ) INFORMATION FOR SEQ ID NO: 43:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:43:

ATCTGTTACC AGCATGTAAT         20

( 2 ) INFORMATION FOR SEQ ID NO: 44:

( i ) SEQUENCE CHARACTERISTICS:
        ( A ) LENGTH: 18
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:44:

CCCTCACTAA ACATACCT         18

( 2 ) INFORMATION FOR SEQ ID NO: 45:

( i ) SEQUENCE CHARACTERISTICS:
        ( A ) LENGTH: 29
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:45:

GATGATGCTG CTGGCATGGG AGTTTCTGG         29

( 2 ) INFORMATION FOR SEQ ID NO: 46:

( i ) SEQUENCE CHARACTERISTICS:
        ( A ) LENGTH: 31
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO: 46:

CTGTCTGCAT CTGAATATGT GCCGTTACCT G          31

( 2 ) INFORMATION FOR SEQ ID NO: 47:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:47:

ATCTTACTTT CCGTGAGAAG          20

( 2 ) INFORMATION FOR SEQ ID NO: 48:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:48:

CTTGGATGTT GAGCTTCCTA          20

( 2 ) INFORMATION FOR SEQ ID NO: 49:

( i ) SEQUENCE CHARACTERISTICS:
        ( A ) LENGTH: 22
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:49:

TTGTGGTAGA CACGGTGGGT AC          22

( 2 ) INFORMATION FOR SEQ ID NO: 50:

( i ) SEQUENCE CHARACTERISTICS:
        ( A ) LENGTH: 22
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:50:

TGATCGCTGA CAAGCTTAGG CT 22

( 2 ) INFORMATION FOR SEQ ID NO: 51:

( i ) SEQUENCE CHARACTERISTICS:
        ( A ) LENGTH: 24
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:51:

CTCAGAGATG AGCCTGCGAC CATT 24

( 2 ) INFORMATION FOR SEQ ID NO: 52:

( i ) SEQUENCE CHARACTERISTICS:
        ( A ) LENGTH: 25
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:52:

GCATTCCCTC CCGTCCTCAT TCTTC 25

( 2 ) INFORMATION FOR SEQ ID NO: 53:

( i ) SEQUENCE CHARACTERISTICS:
        ( A ) LENGTH: 24
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:53:

GATAGCGAGC ACAAAGAGAG CTAA 24

( 2 ) INFORMATION FOR SEQ ID NO: 54:

( i ) SEQUENCE CHARACTERISTICS:
        ( A ) LENGTH: 36
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:54:

TTCACATCTG TTTGCAAAAC ACGGTCGAAA ACAAAG 36

( 2 ) INFORMATION FOR SEQ ID NO: 55:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:55:

GTTGTTCATG AAGGCCTACT 20

( 2 ) INFORMATION FOR SEQ ID NO: 56:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:56:

TGCATAACCT ACGGTGTGTT 20

( 2 ) INFORMATION FOR SEQ ID NO: 57:

( i ) SEQUENCE CHARACTERISTICS:
        ( A ) LENGTH: 21
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:57:

GAAGCTTATG GTACAGGTTG G 21

( 2 ) INFORMATION FOR SEQ ID NO: 58:

( i ) SEQUENCE CHARACTERISTICS:

( A ) LENGTH: 20
            ( B ) TYPE: nucleic acid
            ( C ) STRANDEDNESS: double
            ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:58:

ATTACCATCC TTGTTGTAAG                                                                                        20

( 2 ) INFORMATION FOR SEQ ID NO: 59:

( i ) SEQUENCE CHARACTERISTICS:
            ( A ) LENGTH: 21
            ( B ) TYPE: nucleic acid
            ( C ) STRANDEDNESS: double
            ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:59:

GGCGAATGGG TGAGTAACAC G                                                                                      21

( 2 ) INFORMATION FOR SEQ ID NO: 60:

( i ) SEQUENCE CHARACTERISTICS:
            ( A ) LENGTH: 22
            ( B ) TYPE: nucleic acid
            ( C ) STRANDEDNESS: double
            ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:60:

CGGATAACGC TTGCGACCTA TG                                                                                     22

( 2 ) INFORMATION FOR SEQ ID NO: 61:

( i ) SEQUENCE CHARACTERISTICS:
            ( A ) LENGTH: 19
            ( B ) TYPE: nucleic acid
            ( C ) STRANDEDNESS: double
            ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:61:

GCTATGAGGA ATCTCGCTG                                                                                         19

( 2 ) INFORMATION FOR SEQ ID NO: 62:

( i ) SEQUENCE CHARACTERISTICS:
        ( A ) LENGTH: 19
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:62:

CTGGCTTCTT CCAGCTTCA                                          19

( 2 ) INFORMATION FOR SEQ ID NO: 63:

( i ) SEQUENCE CHARACTERISTICS:
        ( A ) LENGTH: 19
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:63:

ATACACGTGG TGGAGGTAC                                          19

( 2 ) INFORMATION FOR SEQ ID NO: 64:

( i ) SEQUENCE CHARACTERISTICS:
        ( A ) LENGTH: 19
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:64:

GCGGGCAATA TCTTGCATC                                          19

( 2 ) INFORMATION FOR SEQ ID NO: 65:

( i ) SEQUENCE CHARACTERISTICS:
        ( A ) LENGTH: 24
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal (x i) SEQUENCE DESCRIPTION: SEQ ID NO:65:

GGTTATTCGA TTTCTAAATC GCCT 24

(2) INFORMATION FOR SEQ ID NO: 66:

(i) SEQUENCE CHARACTERISTICS:
  (A) LENGTH: 24
  (B) TYPE: nucleic acid
  (C) STRANDEDNESS: double
  (D) TOPOLOGY: linear (i i) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:66:

GGACTATTGT CTAAACAATT TCCC 24

(2) INFORMATION FOR SEQ ID NO: 67:

(i) SEQUENCE CHARACTERISTICS:
  (A) LENGTH: 18
  (B) TYPE: nucleic acid
  (C) STRANDEDNESS: double
  (D) TOPOLOGY: linear (i i) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:67:

AGTTTGATCA TGGCTCAG 18

(2) INFORMATION FOR SEQ ID NO: 68:

(i) SEQUENCE CHARACTERISTICS:
  (A) LENGTH: 21
  (B) TYPE: nucleic acid
  (C) STRANDEDNESS: double
  (D) TOPOLOGY: linear (i i) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:68:

GAGTTTGCCG GGACTTCTTC T 21

(2) INFORMATION FOR SEQ ID NO: 69:

(i) SEQUENCE CHARACTERISTICS:
  (A) LENGTH: 30
  (B) TYPE: nucleic acid
  (C) STRANDEDNESS: double
  (D) TOPOLOGY: linear (i i) MOLECULE TYPE: other nucleic acid (i i i) HYPOTHETICAL: no (iv) ANTI-SENSE: yes (v) FRAGMENT TYPE: internal (xi) SEQUENCE DESCRIPTION: SEQ ID NO:69:

AGTTGGAGGA CATCAAGCAG CCATGCAAAT 30

(2) INFORMATION FOR SEQ ID NO: 70:

(i) SEQUENCE CHARACTERISTICS:
        (A) LENGTH: 27
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:70:

TGCTATGTCA GTTCCCCTTG GTTCTCT 27

(2) INFORMATION FOR SEQ ID NO: 71:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:71:

CCCGGGCCCC CTGACTTGTC 20

(2) INFORMATION FOR SEQ ID NO: 72:

(i) SEQUENCE CHARACTERISTICS:
        (A) LENGTH: 21
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:72:

GCTTTCACTG TCCCACAGCA G 21

(2) INFORMATION FOR SEQ ID NO: 73:

(i) SEQUENCE CHARACTERISTICS:
        (A) LENGTH: 20
        (B) TYPE: nucleic acid
        (C) STRANDEDNESS: double
        (D) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:73:

CAAGGTATGT TGCCCGTTTG 20

( 2 ) INFORMATION FOR SEQ ID NO: 74:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:74:

AAAGCCCTGC GAACCACTGA 20

( 2 ) INFORMATION FOR SEQ ID NO: 75:

( i ) SEQUENCE CHARACTERISTICS:
        ( A ) LENGTH: 19
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:75:

CCCAACACTA CTCGGCTAG 19

( 2 ) INFORMATION FOR SEQ ID NO: 76:

( i ) SEQUENCE CHARACTERISTICS:
        ( A ) LENGTH: 24
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:76:

AACTACTGTC TTCACGCAGA AAGC 24

( 2 ) INFORMATION FOR SEQ ID NO: 77:

( i ) SEQUENCE CHARACTERISTICS:
        ( A ) LENGTH: 22

(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:77:

TACATCGGCG TCATCTGCGG GG                      22

(2) INFORMATION FOR SEQ ID NO: 78:

(i) SEQUENCE CHARACTERISTICS:
    (A) LENGTH: 22
    (B) TYPE: nucleic acid
    (C) STRANDEDNESS: double
    (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:78:

CAGTTCGGCG GTGAGGACAA AG                      22

(2) INFORMATION FOR SEQ ID NO: 79:

(i) SEQUENCE CHARACTERISTICS:
    (A) LENGTH: 25
    (B) TYPE: nucleic acid
    (C) STRANDEDNESS: double
    (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:79:

AAGCTTGCAC AATGCCAAAA AACAG                   25

(2) INFORMATION FOR SEQ ID NO: 80:

(i) SEQUENCE CHARACTERISTICS:
    (A) LENGTH: 25
    (B) TYPE: nucleic acid
    (C) STRANDEDNESS: double
    (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:80:

CTCGAGTATG CCGAGACCCC TAATC                   25

( 2 ) INFORMATION FOR SEQ ID NO: 81:

( i ) SEQUENCE CHARACTERISTICS:
    ( A ) LENGTH: 26
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:81:

TATCCCAGCT GTTTTCATAT AGTAAC                      26

( 2 ) INFORMATION FOR SEQ ID NO: 82:

( i ) SEQUENCE CHARACTERISTICS:
    ( A ) LENGTH: 26
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:82:

GCCTTGCGGT AGCACTAGAT TTTTTG                      26

( 2 ) INFORMATION FOR SEQ ID NO: 83:

( i ) SEQUENCE CHARACTERISTICS:
    ( A ) LENGTH: 20
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:83:

AAGGATGCCT GGACACAAGA                         20

( 2 ) INFORMATION FOR SEQ ID NO: 84:

( i ) SEQUENCE CHARACTERISTICS:
    ( A ) LENGTH: 22
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:84:

TGGTGCTGCT GGTGGTGGCA AT 22

(2) INFORMATION FOR SEQ ID NO: 85:

(i) SEQUENCE CHARACTERISTICS:
        (A) LENGTH: 25
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:85:

CCTAGTGTGG ATGACCTACG GGCCA 25

(2) INFORMATION FOR SEQ ID NO: 86:

(i) SEQUENCE CHARACTERISTICS:
        (A) LENGTH: 25
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:86:

CAGACACAGT GTCCTCCCGC TCCTC 25

(2) INFORMATION FOR SEQ ID NO: 87:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:87:

ATGTCCGTAC AACATCAACT 20

(2) INFORMATION FOR SEQ ID NO: 88:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:88:

CGATTTTCCA AGAGAGACGC 20

(2) INFORMATION FOR SEQ ID NO: 89:

(i) SEQUENCE CHARACTERISTICS:
(A) LENGTH: 20
(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:89:

AGTCTTTAGG GTCTTCTACC 20

(2) INFORMATION FOR SEQ ID NO: 90:

(i) SEQUENCE CHARACTERISTICS:
(A) LENGTH: 20
(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:90:

GGTGCCAACC TATGGAACAG 20

(2) INFORMATION FOR SEQ ID NO: 91:

(i) SEQUENCE CHARACTERISTICS:
(A) LENGTH: 22
(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:91:

GGAACAGACT TAGAGCTTAT TC 22

(2) INFORMATION FOR SEQ ID NO: 92:

(i) SEQUENCE CHARACTERISTICS:
(A) LENGTH: 21
(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:92:

GCTTGTGTAA GTCTTCACTA G                                             21

(2) INFORMATION FOR SEQ ID NO: 93:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:93:

CAATAGCTGG TTTTATAGAA                                               20

(2) INFORMATION FOR SEQ ID NO: 94:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:94:

TTATCATACA GATTCTTGAC                                               20

(2) INFORMATION FOR SEQ ID NO: 95:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:95:

GAAGGCAAAG CAGAACTAGC                                               20

(2) INFORMATION FOR SEQ ID NO: 96:

(i) SEQUENCE CHARACTERISTICS:
        (A) LENGTH: 20
        (B) TYPE: nucleic acid (C) STRANDEDNESS: double
            (D) TOPOLOGY: linear (i i) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:96:

TGGCCTTCTG CTATTTCAAA 20

(2) INFORMATION FOR SEQ ID NO: 97:

(i) SEQUENCE CHARACTERISTICS:
            (A) LENGTH: 20
            (B) TYPE: nucleic acid
            (C) STRANDEDNESS: double
            (D) TOPOLOGY: linear (i i) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:97:

GTGCAAACTG CATCTTGTGG 20

(2) INFORMATION FOR SEQ ID NO: 98:

(i) SEQUENCE CHARACTERISTICS:
            (A) LENGTH: 20
            (B) TYPE: nucleic acid
            (C) STRANDEDNESS: double
            (D) TOPOLOGY: linear (i i) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:98:

CTCATTTCTT GATCTCCATG 20

(2) INFORMATION FOR SEQ ID NO: 99:

(i) SEQUENCE CHARACTERISTICS:
            (A) LENGTH: 20
            (B) TYPE: nucleic acid
            (C) STRANDEDNESS: double
            (D) TOPOLOGY: linear (i i) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:99:

GGACCAAGAG AAAACGTAGC 20

(2) INFORMATION FOR SEQ ID NO: 100:

( i ) SEQUENCE CHARACTERISTICS:
 ( A ) LENGTH: 27
 ( B ) TYPE: nucleic acid
 ( C ) STRANDEDNESS: double
 ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:100:

GGTCACATCA TACAATTCTA ATCTAAG 27

( 2 ) INFORMATION FOR SEQ ID NO: 101:

( i ) SEQUENCE CHARACTERISTICS:
  ( A ) LENGTH: 26
  ( B ) TYPE: nucleic acid
  ( C ) STRANDEDNESS: double
  ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:101:

ATGACTTTTG AGGTGGATCC CATGGA 26

( 2 ) INFORMATION FOR SEQ ID NO: 102:

( i ) SEQUENCE CHARACTERISTICS:
  ( A ) LENGTH: 23
  ( B ) TYPE: nucleic acid
  ( C ) STRANDEDNESS: double
  ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:102:

GCCGAGAAGG GCGTGCGCAG GTA 23

( 2 ) INFORMATION FOR SEQ ID NO: 103:

( i ) SEQUENCE CHARACTERISTICS:
  ( A ) LENGTH: 24
  ( B ) TYPE: nucleic acid
  ( C ) STRANDEDNESS: double
  ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO: 103:

```
TGCTTTGCCC CATGGGACCT CGAG                                                    24
```

( 2 ) INFORMATION FOR SEQ ID NO: 104:

( i ) SEQUENCE CHARACTERISTICS:
        ( A ) LENGTH: 21
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:104:

```
GGCGAACACG CTCATCACGG T                                                       21
```

( 2 ) INFORMATION FOR SEQ ID NO: 105:

( i ) SEQUENCE CHARACTERISTICS:
        ( A ) LENGTH: 25
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:105:

```
CCTCCGGCCC CTGAATGCGG CTAAT                                                   25
```

( 2 ) INFORMATION FOR SEQ ID NO: 106:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:106:

```
ATTGTCACCA TAAGCAGCCA                                                         20
```

( 2 ) INFORMATION FOR SEQ ID NO: 107:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:107:

GCMCAGGGWC ATAAYAATGG 20

( 2 ) INFORMATION FOR SEQ ID NO: 108:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO: 108:

CGTCCMAARG GAWACTGATC 20

( 2 ) INFORMATION FOR SEQ ID NO: 109:

( i ) SEQUENCE CHARACTERISTICS:
        ( A ) LENGTH: 26
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:109:

CACTGAATAA GAGGATACAA GAATGG 26

( 2 ) INFORMATION FOR SEQ ID NO: 110:

( i ) SEQUENCE CHARACTERISTICS:
        ( A ) LENGTH: 23
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:110:

GGAGGAATAT TACATGTGCC TTT 23

( 2 ) INFORMATION FOR SEQ ID NO: 111:

( i ) SEQUENCE CHARACTERISTICS:
        ( A ) LENGTH: 19
        ( B ) TYPE: nucleic acid
        ( C ) STRANDEDNESS: double
        ( D ) TOPOLOGY: linear ( i i ) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:111:

TCCGTAGGTG AACCTGCGA 19

(2) INFORMATION FOR SEQ ID NO: 112:

(i) SEQUENCE CHARACTERISTICS:
      (A) LENGTH: 20
      (B) TYPE: nucleic acid
      (C) STRANDEDNESS: double
      (D) TOPOLOGY: linear (i i) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:112:

TCCTCCGCTT ATTGATATGC 20

(2) INFORMATION FOR SEQ ID NO: 113:

(i) SEQUENCE CHARACTERISTICS:
      (A) LENGTH: 20
      (B) TYPE: nucleic acid
      (C) STRANDEDNESS: double
      (D) TOPOLOGY: linear (i i) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:113:

AGTTACGGCC ATACCTCAGA 20

(2) INFORMATION FOR SEQ ID NO: 114:

(i) SEQUENCE CHARACTERISTICS:
      (A) LENGTH: 20
      (B) TYPE: nucleic acid
      (C) STRANDEDNESS: double
      (D) TOPOLOGY: linear (i i) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:114:

AAAGCTACAG CACGTCGTAT 20

(2) INFORMATION FOR SEQ ID NO: 115:

(i) SEQUENCE CHARACTERISTICS:
      (A) LENGTH: 21
      (B) TYPE: nucleic acid
      (C) STRANDEDNESS: double (D) TOPOLOGY: linear (i i) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:115:

GCAAGTCTGG TGCCAGCAGC C                                21

(2) INFORMATION FOR SEQ ID NO: 116:

(i) SEQUENCE CHARACTERISTICS:
        (A) LENGTH: 27
        (B) TYPE: nucleic acid
        (C) STRANDEDNESS: double
        (D) TOPOLOGY: linear (i i) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:116:

CCGTCAATTC CTTTATGTTT CAGCCTT                          27

(2) INFORMATION FOR SEQ ID NO: 117:

(i) SEQUENCE CHARACTERISTICS:
        (A) LENGTH: 26
        (B) TYPE: nucleic acid
        (C) STRANDEDNESS: double
        (D) TOPOLOGY: linear (i i) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:117:

AAATAATGKA CGGGTGAGAT GCATGA                           26

(2) INFORMATION FOR SEQ ID NO: 118:

(i) SEQUENCE CHARACTERISTICS:
        (A) LENGTH: 21
        (B) TYPE: nucleic acid
        (C) STRANDEDNESS: double
        (D) TOPOLOGY: linear (i i) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:118:

GGGTTCGATT GGGGTTGGTG T                                21

(2) INFORMATION FOR SEQ ID NO: 119:

( i ) SEQUENCE CHARACTERISTICS:
    ( A ) LENGTH: 18
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:119:

GTGGGGGAGG GGCGTTCT                                                         18

( 2 ) INFORMATION FOR SEQ ID NO: 120:

( i ) SEQUENCE CHARACTERISTICS:
        ( A ) LENGTH: 21
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:120:

ATTTTACACC AACCCCCAGT T                                                     21

( 2 ) INFORMATION FOR SEQ ID NO: 121:

( i ) SEQUENCE CHARACTERISTICS:
        ( A ) LENGTH: 24
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:121:

GGATAACTAC GGAAAAGCTG TAGC                                                  24

( 2 ) INFORMATION FOR SEQ ID NO: 122:

( i ) SEQUENCE CHARACTERISTICS:
        ( A ) LENGTH: 27
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO: 122:

CGACTTCTCC TTCCTTTAAA AGATAGG                                               27

( 2 ) INFORMATION FOR SEQ ID NO: 123:

( i ) SEQUENCE CHARACTERISTICS:
        ( A ) LENGTH: 32
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( i x ) FEATURE:
        ( D ) OTHER INFORMATION: Maximum fragment size: about 500 nt ( x i ) SEQUENCE DESCRIPTION: SEQ ID NO:123:

GTTCAAGATT AATAATTGCA ATAATCTATC CC    32

( 2 ) INFORMATION FOR SEQ ID NO: 124:

( i ) SEQUENCE CHARACTERISTICS:
        ( A ) LENGTH: 24
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:124:

GGCCAATTCA TTCAATGAAT TGAG    24

( 2 ) INFORMATION FOR SEQ ID NO: 125:

( i ) SEQUENCE CHARACTERISTICS:
        ( A ) LENGTH: 25
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:125:

CTCAGATCTA GAAACAATGC TTCTC    25

( 2 ) INFORMATION FOR SEQ ID NO: 126:

( i ) SEQUENCE CHARACTERISTICS:
        ( A ) LENGTH: 23
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no (iv) ANTI-SENSE: yes (v) FRAGMENT TYPE: internal (xi) SEQUENCE DESCRIPTION: SEQ ID NO:126:

CTTAGTATAA GCTTTTATAC AGC                                                                                    23

(2) INFORMATION FOR SEQ ID NO: 127:

(i) SEQUENCE CHARACTERISTICS:
    (A) LENGTH: 25
    (B) TYPE: nucleic acid
    (C) STRANDEDNESS: double
    (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO: 127:

ATAGGTCAGA AACTTGAATG ATACA                                                                                  25

(2) INFORMATION FOR SEQ ID NO: 128:

(i) SEQUENCE CHARACTERISTICS:
    (A) LENGTH: 20
    (B) TYPE: nucleic acid
    (C) STRANDEDNESS: double
    (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:128:

GCGCACCAGG AATGTCTTGT                                                                                        20

(2) INFORMATION FOR SEQ ID NO: 129:

(i) SEQUENCE CHARACTERISTICS:
    (A) LENGTH: 20
    (B) TYPE: nucleic acid
    (C) STRANDEDNESS: double
    (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:129:

TCACCTACGG ATACCTTGTT                                                                                        20

(2) INFORMATION FOR SEQ ID NO: 130:

(i) SEQUENCE CHARACTERISTICS:
    (A) LENGTH: 26
    (B) TYPE: nucleic acid
    (C) STRANDEDNESS: double
    (D) TOPOLOGY: linear (i i) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:130:

CCGAGTTTGA TCCAAAAAGT TACGAA 26

(2) INFORMATION FOR SEQ ID NO: 131:

(i) SEQUENCE CHARACTERISTICS:
(A) LENGTH: 26
(B) TYPE: nucleic acid
(C) STRANDEDNESS: double
(D) TOPOLOGY: linear (i i) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:131:

TAGCTCCTCA TATGCCTTAT TGAGTA 26

(2) INFORMATION FOR SEQ ID NO: 132:

(i) SEQUENCE CHARACTERISTICS:
(A) LENGTH: 26
(B) TYPE: nucleic acid
(C) STRANDEDNESS: double
(D) TOPOLOGY: linear (i i) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:132:

GGAATTCCTT CCGAGCTTCG CTGCGT 26

(2) INFORMATION FOR SEQ ID NO: 133:

(i) SEQUENCE CHARACTERISTICS:
(A) LENGTH: 28
(B) TYPE: nucleic acid
(C) STRANDEDNESS: double
(D) TOPOLOGY: linear (i i) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:133:

CGGGATCCCG TCTTCAAACC CCCTACTG 28

(2) INFORMATION FOR SEQ ID NO: 134:

(i) SEQUENCE CHARACTERISTICS:
(A) LENGTH: 22

( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:134:

CGGGCAGATT CTAGACCTCC TG 22

( 2 ) INFORMATION FOR SEQ ID NO: 135:

( i ) SEQUENCE CHARACTERISTICS:
        ( A ) LENGTH: 23
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:135:

CGATGATCTT GGAGCATTCC CAC 23

( 2 ) INFORMATION FOR SEQ ID NO: 136:

( i ) SEQUENCE CHARACTERISTICS:
        ( A ) LENGTH: 26
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:136:

CTTGACTCTT CAAAAGAGAA AATTAC 26

( 2 ) INFORMATION FOR SEQ ID NO: 137:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:137:

TCTCTATRTG CAYACGGAGC 20

( 2 ) INFORMATION FOR SEQ ID NO: 138:

( i ) SEQUENCE CHARACTERISTICS:
        ( A ) LENGTH: 19
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO: 138:

CCATACTGAT TGCCGCAAT 19

( 2 ) INFORMATION FOR SEQ ID NO: 139:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:139:

CTTCGGTATC CTATTCCCGG 20

( 2 ) INFORMATION FOR SEQ ID NO: 140:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:140:

GGATGCATCT CTGGTCATTG 20

( 2 ) INFORMATION FOR SEQ ID NO: 141:

( i ) SEQUENCE CHARACTERISTICS:
        ( A ) LENGTH: 18
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:141:

CTGGATGGTA TGGTGAGG                                                                18

(2) INFORMATION FOR SEQ ID NO: 142:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:142:

GGAGGCCAAC AATTATTTCC                                                              20

(2) INFORMATION FOR SEQ ID NO: 143:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:143:

TAACAAACCG ATAATGGCGC                                                              20

(2) INFORMATION FOR SEQ ID NO: 144:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:144:

CATCTTGTTA GAGGGATTGG                                                              20

(2) INFORMATION FOR SEQ ID NO: 145:

(i) SEQUENCE CHARACTERISTICS:
        (A) LENGTH: 22
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (x i) SEQUENCE DESCRIPTION: SEQ ID NO:145:

CTCTTGAAAC TGGGAGACTT GA                                    22

(2) INFORMATION FOR SEQ ID NO: 146:

(i) SEQUENCE CHARACTERISTICS:
        (A) LENGTH: 20
        (B) TYPE: nucleic acid
        (C) STRANDEDNESS: double
        (D) TOPOLOGY: linear (i i) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:146:

CCGTCAATTC MTTTRAGTTT                                       20

(2) INFORMATION FOR SEQ ID NO: 147:

(i) SEQUENCE CHARACTERISTICS:
        (A) LENGTH: 21
        (B) TYPE: nucleic acid
        (C) STRANDEDNESS: double
        (D) TOPOLOGY: linear (i i) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:147:

GGTGGAGCTT CAATTGGAGA G                                     21

(2) INFORMATION FOR SEQ ID NO: 148:

(i) SEQUENCE CHARACTERISTICS:
        (A) LENGTH: 25
        (B) TYPE: nucleic acid
        (C) STRANDEDNESS: double
        (D) TOPOLOGY: linear (i i) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:148:

GTGTAACCTA CTTTCATAAC ACCAG                                 25

(2) INFORMATION FOR SEQ ID NO: 149:

(i) SEQUENCE CHARACTERISTICS:
        (A) LENGTH: 20
        (B) TYPE: nucleic acid
        (C) STRANDEDNESS: double
        (D) TOPOLOGY: linear (i i) MOLECULE TYPE: other nucleic acid (  i  i  i  ) HYPOTHETICAL: no (  i  v  ) ANTI-SENSE: yes (  v  ) FRAGMENT TYPE: internal (  x  i  ) SEQUENCE DESCRIPTION: SEQ ID NO: 149:

TTGGAAACGG TTAAAACGAA                    20

( 2 ) INFORMATION FOR SEQ ID NO: 150:

( i ) SEQUENCE CHARACTERISTICS:
            ( A ) LENGTH: 20
            ( B ) TYPE: nucleic acid
            ( C ) STRANDEDNESS: double
            ( D ) TOPOLOGY: linear (  i  i  ) MOLECULE TYPE: other nucleic acid (  i  i  i  ) HYPOTHETICAL: no (  i  v  ) ANTI-SENSE: no (  v  ) FRAGMENT TYPE: internal (  x  i  ) SEQUENCE DESCRIPTION: SEQ ID NO:150:

GAACCTTCCC ATCAAAAACA                    20

( 2 ) INFORMATION FOR SEQ ID NO: 151:

( i ) SEQUENCE CHARACTERISTICS:
            ( A ) LENGTH: 20
            ( B ) TYPE: nucleic acid
            ( C ) STRANDEDNESS: double
            ( D ) TOPOLOGY: linear (  i  i  ) MOLECULE TYPE: other nucleic acid (  i  i  i  ) HYPOTHETICAL: no (  i  v  ) ANTI-SENSE: yes (  v  ) FRAGMENT TYPE: internal (  x  i  ) SEQUENCE DESCRIPTION: SEQ ID NO:151:

TCGCATCAAA CTGACAAACG                    20

( 2 ) INFORMATION FOR SEQ ID NO: 152:

( i ) SEQUENCE CHARACTERISTICS:
            ( A ) LENGTH: 20
            ( B ) TYPE: nucleic acid
            ( C ) STRANDEDNESS: double
            ( D ) TOPOLOGY: linear (  i  i  ) MOLECULE TYPE: other nucleic acid (  i  i  i  ) HYPOTHETICAL: no (  i  v  ) ANTI-SENSE: no (  v  ) FRAGMENT TYPE: internal (  x  i  ) SEQUENCE DESCRIPTION: SEQ ID NO:152:

GCAGGTACTC TATAAGTGCC                    20

( 2 ) INFORMATION FOR SEQ ID NO: 153:

( i ) SEQUENCE CHARACTERISTICS:
            ( A ) LENGTH: 20
            ( B ) TYPE: nucleic acid (C) STRANDEDNESS: double
(D) TOPOLOGY: linear (i i) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:153:

GACATAAAAG CTAGGAATTT 20

(2) INFORMATION FOR SEQ ID NO: 154:

(i) SEQUENCE CHARACTERISTICS:
(A) LENGTH: 20
(B) TYPE: nucleic acid
(C) STRANDEDNESS: double
(D) TOPOLOGY: linear (i i) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:154:

AAATCGGATT AACATTATCC 20

(2) INFORMATION FOR SEQ ID NO: 155:

(i) SEQUENCE CHARACTERISTICS:
(A) LENGTH: 20
(B) TYPE: nucleic acid
(C) STRANDEDNESS: double
(D) TOPOLOGY: linear (i i) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:155:

CTAGTTTGGT AATATCTCCT 20

(2) INFORMATION FOR SEQ ID NO: 156:

(i) SEQUENCE CHARACTERISTICS:
(A) LENGTH: 20
(B) TYPE: nucleic acid
(C) STRANDEDNESS: double
(D) TOPOLOGY: linear (i i) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:156:

TAATGCTATA TCTTATAGGG 20

(2) INFORMATION FOR SEQ ID NO: 157:

( i ) SEQUENCE CHARACTERISTICS:
( A ) LENGTH: 20
( B ) TYPE: nucleic acid
( C ) STRANDEDNESS: double
( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:157:

TAGATAAAGT TAAAACAAGC 20

( 2 ) INFORMATION FOR SEQ ID NO: 158:

( i ) SEQUENCE CHARACTERISTICS:
( A ) LENGTH: 20
( B ) TYPE: nucleic acid
( C ) STRANDEDNESS: double
( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:158:

TAACTTACCG TGGACCCTTC 20

( 2 ) INFORMATION FOR SEQ ID NO: 159:

( i ) SEQUENCE CHARACTERISTICS:
( A ) LENGTH: 20
( B ) TYPE: nucleic acid
( C ) STRANDEDNESS: double
( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:159:

ATGGCAGCAT CAGCTTGATA 20

( 2 ) INFORMATION FOR SEQ ID NO: 160:

( i ) SEQUENCE CHARACTERISTICS:
( A ) LENGTH: 20
( B ) TYPE: nucleic acid
( C ) STRANDEDNESS: double
( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:160:

TTTCCAATAA CCACCCGTTT                                                                                      20

( 2 ) INFORMATION FOR SEQ ID NO: 161:

( i ) SEQUENCE CHARACTERISTICS:
    ( A ) LENGTH: 20
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:161:

CTAGTGCATT TGTTATTCAA                                                                                      20

( 2 ) INFORMATION FOR SEQ ID NO: 162:

( i ) SEQUENCE CHARACTERISTICS:
    ( A ) LENGTH: 20
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:162:

TGCATTGACA CCATAGTACT                                                                                      20

( 2 ) INFORMATION FOR SEQ ID NO: 163:

( i ) SEQUENCE CHARACTERISTICS:
    ( A ) LENGTH: 20
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:163:

ACGGCTATAT ACATTCAATT                                                                                      20

( 2 ) INFORMATION FOR SEQ ID NO: 164:

( i ) SEQUENCE CHARACTERISTICS:
    ( A ) LENGTH: 20
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL: no ( i v ) ANTI-SENSE: no (v) FRAGMENT TYPE: internal (xi) SEQUENCE DESCRIPTION: SEQ ID NO:164:

TCCATCGATA ATATACCTAA 20

(2) INFORMATION FOR SEQ ID NO: 165:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:165:

AACTGGAGGA AGGTGGGGAT 20

(2) INFORMATION FOR SEQ ID NO: 166:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (xi) SEQUENCE DESCRIPTION: SEQ ID NO:166:

AGGAGGTGAT CCAACCGCA 19

(2) INFORMATION FOR SEQ ID NO: 167:

(i) SEQUENCE CHARACTERISTICS:
        (A) LENGTH: 15
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (xi) SEQUENCE DESCRIPTION: SEQ ID NO:167:

CCACCTTGAC TATTT 15

(2) INFORMATION FOR SEQ ID NO: 168:

(i) SEQUENCE CHARACTERISTICS:
        (A) LENGTH: 15
        (B) TYPE: nucleic acid
        (C) STRANDEDNESS: double
        (D) TOPOLOGY: linear (ii) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:168:

TTAATTAGGA GGTAA 15

(2) INFORMATION FOR SEQ ID NO: 169:

(i) SEQUENCE CHARACTERISTICS:
  (A) LENGTH: 26
  (B) TYPE: nucleic acid
  (C) STRANDEDNESS: double
  (D) TOPOLOGY: linear (i i) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:169:

CGTGGAGGCG ATCACACCGC AGACGT 26

(2) INFORMATION FOR SEQ ID NO: 170:

(i) SEQUENCE CHARACTERISTICS:
  (A) LENGTH: 27
  (B) TYPE: nucleic acid
  (C) STRANDEDNESS: double
  (D) TOPOLOGY: linear (i i) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:170:

AGTGCGACGG GTGCACGTCG CGGACCT 27

(2) INFORMATION FOR SEQ ID NO: 171:

(i) SEQUENCE CHARACTERISTICS:
  (A) LENGTH: 35
  (B) TYPE: nucleic acid
  (C) STRANDEDNESS: double
  (D) TOPOLOGY: linear (i i) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:171:

TTGGTTGCAC TTTAAATTTT CCCATTAGTC CTATT 35

(2) INFORMATION FOR SEQ ID NO: 172:

(i) SEQUENCE CHARACTERISTICS:
  (A) LENGTH: 35
  (B) TYPE: nucleic acid
  (C) STRANDEDNESS: double ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:172:

CCTACTAACT TCTGTATGTC ATTGACAGTC CAGCT 35

( 2 ) INFORMATION FOR SEQ ID NO: 173:

( i ) SEQUENCE CHARACTERISTICS:
        ( A ) LENGTH: 23
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:173:

GARATNGGNN NNGGNAARGG NCA 23

( 2 ) INFORMATION FOR SEQ ID NO: 174:

( i ) SEQUENCE CHARACTERISTICS:
        ( A ) LENGTH: 17
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:174:

AAYTGRTTYT TNGTRAA 17

( 2 ) INFORMATION FOR SEQ ID NO: 175:

( i ) SEQUENCE CHARACTERISTICS:
        ( A ) LENGTH: 22
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:175:

AAAATCGATG GTAAAGGTTG GC 22

( 2 ) INFORMATION FOR SEQ ID NO: 176:

( i ) SEQUENCE CHARACTERISTICS:
    ( A ) LENGTH: 22
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:176:

AGTTCTGCAG TACCGGATTT GC      22

( 2 ) INFORMATION FOR SEQ ID NO: 177:

( i ) SEQUENCE CHARACTERISTICS:
    ( A ) LENGTH: 17
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:177:

AGTTATCTAC ACGACGG      17

( 2 ) INFORMATION FOR SEQ ID NO: 178:

( i ) SEQUENCE CHARACTERISTICS:
    ( A ) LENGTH: 17
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:178:

GGCGTACTAT TCACTCT      17

( 2 ) INFORMATION FOR SEQ ID NO: 179:

( i ) SEQUENCE CHARACTERISTICS:
    ( A ) LENGTH: 20
    ( B ) TYPE: nucleic acid
    ( C ) STRANDEDNESS: double
    ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:179:

ACCTACTCCC AACATCAGCC      20

( 2 ) INFORMATION FOR SEQ ID NO: 180:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:180:

ATATAGATCT CACTACGCGC     20

( 2 ) INFORMATION FOR SEQ ID NO: 181:

( i ) SEQUENCE CHARACTERISTICS:
        ( A ) LENGTH: 17
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:181:

AGAGAATTAT GCAGTGC     17

( 2 ) INFORMATION FOR SEQ ID NO: 182:

( i ) SEQUENCE CHARACTERISTICS:
        ( A ) LENGTH: 22
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:182:

GACAGTTACC AATGCTTAAT CA     22

( 2 ) INFORMATION FOR SEQ ID NO: 183:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:183:

CAGCTACATC GACTATGCGA 20

( 2 ) INFORMATION FOR SEQ ID NO: 184:

( i ) SEQUENCE CHARACTERISTICS:
        ( A ) LENGTH: 19
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:184:

GGGCTTCGGT GTACCTCAT 19

( 2 ) INFORMATION FOR SEQ ID NO: 185:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: yes ( v ) FRAGMENT TYPE: internal ( x i ) SEQUENCE DESCRIPTION: SEQ ID NO:185:

AGCTCGTATG GCACCGGAAC 20

( 2 ) INFORMATION FOR SEQ ID NO: 186:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no ( i v ) ANTI-SENSE: no ( v ) FRAGMENT TYPE: internal ( x i ) SEQUENCE DESCRIPTION: SEQ ID NO:186:

TTGACCTCCC ACCCGACTTG 20

( 2 ) INFORMATION FOR SEQ ID NO: 187:

( i ) SEQUENCE CHARACTERISTICS:
        ( A ) LENGTH: 23
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL: no (i v) ANTI-SENSE: yes (v) FRAGMENT TYPE: internal (x i) SEQUENCE DESCRIPTION: SEQ ID NO:187:

CATCGCCGTC CCCGAATTTC AAA                                                    23

(2) INFORMATION FOR SEQ ID NO: 188:

(i) SEQUENCE CHARACTERISTICS:
    (A) LENGTH: 21
    (B) TYPE: nucleic acid
    (C) STRANDEDNESS: double
    (D) TOPOLOGY: linear (i i) MOLECULE TYPE: other nucleic acid (i i i) HYPOTHETICAL: no (i v) ANTI-SENSE: no (v) FRAGMENT TYPE: internal (x i) SEQUENCE DESCRIPTION: SEQ ID NO:188:

GATGCGGAAG ATACCGTGGC T                                                      21

(2) INFORMATION FOR SEQ ID NO: 189:

(i) SEQUENCE CHARACTERISTICS:
    (A) LENGTH: 24
    (B) TYPE: nucleic acid
    (C) STRANDEDNESS: double
    (D) TOPOLOGY: linear (i i) MOLECULE TYPE: other nucleic acid (i i i) HYPOTHETICAL: no (i v) ANTI-SENSE: yes (v) FRAGMENT TYPE: internal (x i) SEQUENCE DESCRIPTION: SEQ ID NO:189:

TTAATAGCAC CCGGTACAAG CAGG                                                   24

METHOD, COMPOSITIONS AND KIT FOR DETECTION AND IDENTIFICATION OF MICROORGANISMS

This application is a continuation-in-part of U.S. patent applications Ser. Nos. 08/684,498, filed Jul. 19, 1996, now U.S. Pat. No. 5,830,657; 08/640,672 filed May 1, 1996, now U.S. Pat. No. 5,789,168; and 08/577,858, filed Dec. 22, 1995, now U.S. Pat. No. 5,834,189; which are incorporated herein by reference.

BACKGROUND OF THE INVENTION

This application relates to a method for detection and identification of microorganisms, including in particular pathogenic microorganisms, and to compositions and kits useful in practicing the method. The invention can be applied to detection of viruses, including HIV and hepatitis, bacteria, including Chlamydia, fungi, including *Cryptococcus neoformans* and protozoa, including *Trypanosoma cruzi*.

Detection of the presence of pathogenic microorganisms through DNA-based technology is emerging as an important tool in the diagnosis of many diseases. For example, diagnosis of *Chlamydia trachomatis* infections, the most common bacterial sexually transmitted disease in North America, is shifting from traditional methods such as culture, enzyme immunoassay (EIA) and direct fluorescent antibodies (DFA) to DNA-hybridization diagnostics. Roche Diagnostic Systems, Inc. (Nutley, N.J.) manufactures Amplicor™, a test which detects *C. trachomatis* and *Neisseria gonorrohoeae* by the hybridization of a pathogen specific probe to PCR amplified products, detectable by a color change/optical density technique. Abbott Laboratories (Abbott Park, Ill.) makes UriProbe, also a test for *C. trachomatis* and *N. gonorrohoeae*, which relies on the ligase chain reaction (LCR). The LCR method, described in Patent Applications WO 9320227, WO 9300447, WO 9408047, WO 9403636, EP 477 972 uses thermostable ligase enzyme to ligate two DNA probes which hybridize in ligatable juxtaposition on a template DNA strand, thus generating a detectable ligated DNA fragment only if the template DNA is present. A multiplex PCR assay for *C. trachomatis* has also been described in Mahony et al., *J. Clin. Microbiol.* 33: 3049–3053 (1995).

A wide variety if infectious pathogens that can be detected by DNA-based methods are listed in *Diagnostic Molecular Microbiology*, Persing et al., eds. American Society for Microbiology, Washington D.C. (1993). This text details diagnostic tests for bacteria, virus, fungi, and protozoa. Diagnostic tests are also proposed for identifying the presence of drug resistance genes or toxin genes.

Although these tests are generally effective for identifying an infectious disease-causing organism if present, they do not routinely provide information concerning the specific serotype, variant or form of the infecting organism. Depending on the organism in question, this information can be significant in determining the likely course of the infection, for determining the most appropriate therapeutic approach and for epidemiological purposes. Furthermore, the previously known assays involve several steps and are therefore more susceptible to systematic error than would be a test with fewer steps. Thus, there remains a need for a simple test format which is generally applicable to the detection of microorganisms, including infectious disease-causing microorganisms, and particularly for a simple test which provides an indication of the specific nature, e.g., the serotype, of the organism. It is an object of the present invention to provide such a test.

It is a further object of the present invention to provide reagent combinations useful in performing tests for infectious disease-causing microorganisms, including Chlamydia human papilloma virus(HPV) and HIV.

It is still a further object of the present invention to provide kits useful in performing tests for infectious disease-causing microorganisms, including Chlamydia, HPV and HIV.

SUMMARY OF THE INVENTION

The present invention provides a method for the evaluation of a sample for the presence of a target microorganism which can be performed directly on a natural abundance DNA preparation obtained from the sample in a single reaction vessel. The method of the invention comprises the steps of:

(a) combining the natural abundance DNA preparation with first and second primers, a nucleotide triphosphate feedstock mixture, a chain-terminating nucleotide triphosphate and a thermally stable polymerase enzyme which incorporates dideoxynucleotides into an extending nucleic acid polymer at a rate which is no less than 0.4 times the rate of incorporation of deoxynucleotides to form a reaction mixture, said first and second primers binding to the sense and antisense strands of the DNA of the target microorganism, respectively, and flanking a selected region within the genome of the target microorganism;

(b) exposing the reaction mixture to a plurality of temperature cycles each of which includes at least a high temperature denaturation phase and a lower temperature extension phase, thereby producing a plurality of species of terminated fragments if DNA from the target microorganism is present in the sample, each species of terminated fragment corresponding to a different incorporation position for the chain-terminating nucleotide triphosphate in the DNA of the target microorganism; and (c) evaluating the terminated fragments produced to determine the incorporation positions of the chain-terminating nucleotide triphosphate. Based on the incorporation positions, not only the presence but also the specific nature, e.g. the serotype, of any target microorganism present can be determined.

DETAILED DESCRIPTION OF THE INVENTION

The present invention provides a novel approach to the evaluation of a sample for the presence of a target microorganism and for the identification of the specific nature of any organism found to be present. The target microorganism may be virus, bacteria, fungi or protozoa. Specific non-limiting examples of microorganisms to which the invention can be suitably applied include bacteria such as *Mycobacteria tuberculosis, Rickettsia rickettsii, Ehrlichia chaffeensis, Borrelia burgdorferi, Yersinia pestis, Treponema pallidum, Chlamydia trachomatis, Chlamydia pneumoniae, Mycoplasma pneumoniae*, Mycoplasma sp., *Legionella pneumophila, Legionella dumoffii, Mycoplasma fermentans*, Ehrlichia sp., *Haemophilus influenzae, Neisseria meningitidis, Streptococcus pneumonia, S. agalactiae*, and *Listeria monocytogenes*; viruses such as Human Immunodeficiency Virus Type 1 (HIV-1), Human T-Cell Lymphotrophic Virus Type 1 (HTLV-1), Hepatitis B Virus (HBV), Hepatitis C Virus (HCV), Herpes Simplex, Herpesvirus 6, Herpesvirus 7, Epstein-Barr Virus, Cytomegalovirus, Varicella-Zoster Virus, JC Virus, Parvovirus B19, Influenza A, B and C, Rotavirus, Human Adenovirus, Rubella Virus, Human Enteroviruses, Genital Human Papillomavirus (HPV), and Hantavirus; fungi such as *Cryptococcus neoformans, Pneumocystis carinii, Histoplasma capsulatum, Blastomyces dermatitidis, Coccidioides immitis,* and *Trichophyton rubrum*; and protozoa such as *Trypanosoma cruzi,* Leishmania sp., Plasmodium, *Entamoeba histolytica, Babesia microti, Giardia lamblia,* Cyclospora sp. and Eimeria sp. The method of the invention may also be used for Cryptosporidium oocyst detection; for identification of bacterial toxin genes, such as the toxin genes from *Vibrio cholerae* 01, enterotoxigenic *Escherichia coli,* Shigella sp., enteroinvasive *E. coli, Helicobacter pylori* (formerly *Campylobacter pylori*), toxigenic *Clostridium difficile, Staphylococcus aureus,* and *Streptococcus pyogenes* exotoxins; and for identification of anti-microbial resistance loci such as rifampin resistance mutations in *Mycobacterium tuberculosis* and *M. leprae*; HIV Drug Resistance, erm Erythromycin Resistance Genes, methicillin-resistance genes in Staphylococcus, Penicillinase-Producing genes in *Neisseria gonorrhoeae,* genes encoding aminoglycoside-modifying enzymes, genes encoding an extended spectrum of Beta-Lactamases, fluoroquinolone and isoniazid resistance mutations in *Mycobacterium tuberculosis,* and genes encoding vancomycin resistance in Enterococci.

In accordance with the method of the invention, a natural abundance DNA-containing sample suspected to contain the target microorganism is combined in a reaction mixture with (1) first and second primers that hybridize with the sense and antisense strands of the DNA of the target microorganism, respectively, and flank a selected region within the genome of the target microorganism, (2) a nucleotide triphosphate feedstock mixture, (3) at least one chain-terminating nucleotide triphosphate and (4) a polymerase enzyme which incorporates dideoxynucleotides into an extending nucleic acid polymer at a rate which is no less than 0.4 times the rate of incorporation of deoxynucleotides to form a reaction mixture. This reaction mixture is processed through a plurality of thermal cycles. Each thermal cycle includes at least an extension step which is performed at a temperature of around 68° to 75 °C. and a denaturation step performed at a temperature of around 90° to 98° C. In addition, the thermal cycles may include a separate annealing step performed at a temperature of 50° to 70° C.

During each cycle, the primers each anneal to the respective strand of any target DNA present in the sample, and primer chain extension using the polymerase enzymes and the nucleotide triphosphate feedstocks proceeds until terminated by incorporation of a chain-terminating nucleotide triphosphate. This results in the production of sequencing fragments comparable to those generated in a conventional sequencing reaction. Analysis of these fragments provides information concerning the sequence of the selected region of the target DNA, and thus of the serotype of the target microorganism. Those extension products which are not terminated prior to reaching the region complementary to the other primer can serve as template for generation of sequencing fragments in later cycles, although this generally occurs to a very small extent.

Among the advantages of the present invention is the ability to perform an evaluation directly on a "natural abundance" DNA sample. The nature of the initial sample will depend on the nature of the target microorganism. For example, in the case of Chlamydia, the initial sample employed in the present invention is suitably a urine sample, genital scraping or genital swab taken from a human patient, although other samples which are suspected of containing Chlamydia can also be tested using the method of the invention. Similarly, to test for HIV infection, the preferred sample is a blood sample.

The initial sample is treated to make DNA in the sample accessible for hybridization with the primers in the reaction mixture, for example by lysis, centrifugation to remove cell debris, and proteolytic digestion to expose the DNA. In accordance with the invention, it is not necessary to perform any type of preferential amplification of the target DNA in the sample prior to the use of the sample in the method of the invention, and indeed to reduce the number of steps and to simplify the assay it is preferred to use sample material which has not been previously subjected to any amplification procedure. As used in the specification and claims hereof, such sample materials in which the DNA in the sample has not been subjected to a preferential amplification step to increase one portion of the DNA relative to the remainder of the DNA will be referred to as "natural abundance samples."

Primers used in the method of the present invention can be any pair of primers which hybridize with the sense and antisense strands DNA of the target microorganism flanking a selected region of diagnostic relevance, and which do not both hybridize to neighboring locations in human DNA or other microbial DNA potentially found in the sample. As used herein, the term "flanking" will be understood to mean the positioning of primers at the 5'-ends of the selected region on each DNA strand, such that extension of the primers leads to replication of the region between the primers. The primers are preferably selected such that the primer pair flanks a region that is about 500 bp or less, although primers spanning larger regions of DNA can be utilized with adjustments to the sequencing mixture (generally an increase in the relative amount of deoxynucleotide triphosphates) to increase the amount of longer sequencing fragments produced.

Primers can be selected to hybridize with highly conserved regions which are the same in all variants of the target microorganism or can be prepared as degenerate primers to take known sequence variations at the primer site into account. Thus, the first and second primers of the invention may each be a discrete oligonucleotide species, or may be a set of oligonucleotide primers with similar but not identical sequences.

Primers can also be selected to bind to the sense and antisense strands of DNA flanking a region of the genome of the target microorganism which is constant across all known variants and forms of the microorganism, in which case the method of the invention would provide detection but not any specific qualitative characterization of the microorganisms, i.e., such primers could not provide discrimination between subspecies, serovars, strains, sub-types, biovars, variants, serotypes or between closely related species of the target microorganism. An example of such a primer pair is a primer pair that binds to the cryptic plasmid of *C. trachomatis* which is recognized as a suitably specific target sequence or detection purposes, but which is not known to vary from strain to strain. Preferably, however, the primers employed will flank a region of the target genome which is variable in sequence depending on the serotype of the organism. Thus, for *C. trachomatis* primers which flank portions of the omp1 gene are preferred. Similarly, in the case of HIV detection, primers flanking known mutation sites in the HIV protease gene or reverse transcriptase gene produce fragments which permit both detection of HIV and the identification of the HIV variant present in the sample. Primers MY09 and MY11 (See example 10) give sequence information for most relevant types of human papilloma virus (HPV) but not other viruses.

In an alternative embodiment, primer pairs are selected which, when treated under the conditions of the invention, give sequence information from a much wider variety of organisms. This is the case with eubacterial "universal" primers such as 91E and 13B listed in Appendix I which can be used to obtain sequence data from the 16S rDNA gene of many bacteria. These primers are useful for identifying which bacterium is present in a septic blood culture, or any other pure but unknown culture. Patient samples which contain a broad range of bacteria will give a complex result, consisting of many overlapping sequences when tested with these primers. The complex result may, in some cases, provide useful information about the bacteria present. However, in the normal course, it is advantageous to separate out the species, i.e. by plating them out first. In this case, individual pure colonies can be selected and identified.

In still another embodiment, the primer pairs are selected to determine whether a specific gene is present in the patient sample. The gene can be a toxin gene, a virulence gene, an anti-biotic resistance gene or a specific mutation which confers drug resistance or the like. Such a test can determine if a micro-organism is present and if it carries the gene at the same time.

Primers for other microorganisms can be derived from known sequence information. Appendix I lists a collection of suitable primer pairs for various other microorganisms which are taken from Persing et al., supra.

One or both of the primers may be labeled with a detectable label at the 5'-end thereof, particularly a fluorescent label such as fluorescein or a cyanine dye such as Cy 5.5. If labels are used on both primers, the labels selected should be spectroscopically-distinct, i.e., they should have either a different excitation spectrum or a different emission spectrum such that one primer can be distinguished from the other. When both primers are labeled with different detectable labels, the sequence of both strands of the sample can be determined in a single reaction.

The nucleotide triphosphate feedstock mixture is a standard mixture of the four conventional bases (A, C, G and T) in a buffer suitable for template-dependent primer extension with the enzyme employed. As will be appreciated by persons skilled in the art, the specific concentrations of the nucleotide triphosphates and the nature of the buffer will vary depending on the enzyme employed. Standard buffers and reagent concentrations for various known polymerase enzymes may be employed in the invention.

The reaction mixture used in the present invention also includes at least one type of chain-terminating nucleotide triphosphate. Separate reactions for the four different types of bases may be run either concurrently or successively. Running all four bases concurrently comports with conventional sequencing practice. However, a preferred embodiment of the present invention combines the single vessel methodology of this application with "single track sequencing" which is described in commonly assigned U.S. patent application Ser. No. 08/577,858. In single track sequencing, the determination of the positions of only one (or in any event less than 4) nucleotide(s) of a target sequence is frequently sufficient to establish the presence of and determine the qualitative nature of a target microorganism by providing a finger-print or bar-code of the target sequence that may be sufficient to distinguish it from all other known varieties of the sequence. Throughput is increased by reducing the number of reactions and electrophoresis runs required to identify a sequence. By selection of the order of bases tested, and intermediate analysis, it may be unnecessary to run all four bases to determine the presence and specific qualitative nature of any target microorganism present in the sample.

The polymerase enzyme used in the invention is a thermostable polymerase enzyme which incorporates dideoxynucleotides into an extending nucleic acid polymer at a rate which is no less than 0.4 times the rate of incorporation of deoxynucleotides. ThermoSequenase™ is exemplary of such an enzyme. Reeve et al., Nature 376: 796–797 (1995). Tabor et al. have also described enzymes which have increased processivity and increased levels of incorporation of dideoxynucleotides. (See EP-A1-0 655 506, which is incorporated herein by reference) Roche sells an enzyme under the trademark TAQ-FS which meets these criteria as well.

The absolute and relative amounts of nucleotide triphosphates and chain-terminating nucleotide triphosphates may be optimized for the particular enzyme employed. In general, however, the nucleotide triphosphates will be included at in the reaction mixture at concentrations of from 250 $\mu$M to 1.5 mM, and the chain-terminating nucleotide triphosphate will be included at a level of from 0.5 $\mu$M to 30 $\mu$M to produce compositions in which the mole ratio of the chain terminating nucleotide triphosphate to the corresponding nucleotide triphosphate is from 1:50 to 1:1000, preferably from 1:100 to 1:500. This will result in incorporation of a chain-terminating nucleotide triphosphate into from 30 to 100 percent of the extending polymer chains formed during the thermal cycling of the reaction mixture.

The method of the invention is suitably practiced using a kit which provides the appropriate reagents in conveniently packaged form. To reduce the number of sample preparation steps, and thus to reduce the risk of erroneous results, such a kit will suitably include at least one pre-prepared mixture comprising all four nucleotide triphosphates and at least one chain terminating nucleotide triphosphate, where the mole ratio of chain terminating nucleotide to the corresponding deoxynucleotide triphosphate is from 1:50 to 1:1000, preferably 1:100 to 1:500.

The invention will now be further described by way of the following non-limiting examples.

EXAMPLE 1

The presence of the sexually transmitted disease pathogen *Chlamydia trachomatis* in a patient sample is detected according to the method of the invention as follows.

Urine samples from patients suspected of carrying a sexually transmitted disease pathogen are prepared for sequence-based diagnosis as follows. 100 ul of first void urine are deposited in a sterile microcentrifuge tube. The tube is centrifuged at 12,000×g for 20 min; the supernatant is removed. 100 ul of Lysis Solution (Proteinase K @ 100 g/ml; 1% Tween 20) is added to the bacterial pellet and incubated 1 h at 55° C., or 18 h at room temperature. After a final incubation at 95° C. for 10 minutes, 200 ul of Geneclean II glass milk is added, according to the manufacturer's instructions. (Bio 101, Inc) DNA is eluted in 10 ul of double distilled $H_2O$. (A lysis solution control may be prepared if desired, by adding the lysis solution to a sterile tube (a tube without any urine pellet), and treating this tube like the others.)

The sample natural abundance DNA is then treated according to the method of the invention with a pair of primers and reagents to identify the sequence of a *C. trachomatis* gene present in the sample, if any. A suitable *C. trachomatis* specific target for sequencing is the cryptic plasmid. Primers that may be used are

| Name | Sequence | |
|---|---|---|
| KL1: | TCCGGAGCGA GTTACGAAGA | [SEQ ID NO: 1] |
| KL2: | ATTCAATGCC CGGGATTGGT | [SEQ ID NO: 2] |

These sequencing primers were employed previously for PCR amplification reactions, but not sequencing (Mahony et al., "Confirmatory polymerase chain reaction testing for *Chlamydia trachomatis* in first void urine from asymptomatic and symptomatic men" *J. Clin Microbiol.* 30: 2241–2245 (1992)).

Either primer may be labeled at the 5'-end with a detectable label such as a Cy5.5 fluorophore. If both primers are labeled, they should be distinguishable. Labels are selected on the basis of the instrument employed for detection. Labeling reactions are performed according to methods well known in the art, such as amidite labeling or dye-ester condensation.

The sequencing reaction mixture is prepared by combining 2.5 ul of the prepared DNA sample, 0.67 ul of 10 uM primer KL1 (labeled with Cy5.5), 0.45 ul of KL2 primer at 10 uM, 2 ul of THERMOSEQUENASE reaction buffer (250 mM Tris-HCl pH 9.0 @25° C., 39 mM $MgCl_2$), 2 ul of THERMOSEQUENASE enzyme (Amersham Life Sciences) diluted 1/10 in the dilution buffer provided with the enzyme and 5.38 ul of double distilled $H_2O$. The final volume is 13 ul.

3 ul of the sequencing reaction mixture is placed in each of 4 clean tubes and covered with one drop of mineral oil (Sigma Chemical Co., Cat # M-5904). The tube is placed in a PTC-100 thermal cycler (M.J. Research, Maine) and heated for 3 min at 94° C., then cooled to 85° C. One of the following termination mixtures are then added to each of the 4 tubes:

3 ul of dNTP:ddATP (1 mM each dNTP, 3.3 uM ddATP) in tube A.

3 ul of dNTP:ddCTP (1 mM each dNTP, 3.3 uM ddCTP) in tube C.

3 ul of dNTP:ddGTP (1 mM each dNTP, 3.3 uM ddGTP) in tube G.

3 ul of dNTP:ddTTP (1 mM each dNTP, 3.3 uM ddTTP) in tube T.

The dNTP:ddNTP mixes are preferably heated to 85° C. when added to the tube. The reaction mixture is mixed well and it is subjected to the following thermal cycling regime for 55 cycles:

94° C./30 sec.

60° C./30 sec.

70° C./1 min

After the last cycle, the tubes are kept at 70° C. for 2 min, then cooled to 4° C. until ready for loading. To view the reaction products, 6 ul of loading buffer (dye/stop solution) is added to each tube. The aqueous phase (the bottom phase disposed under the oil layer) is removed and put it in another tube. The sample is heated to 75° C. for 3 min, and put on ice. 2 ul of each sample is loaded in each well of a MicroGene Blaster automated DNA sequencer (Visible Genetics Inc., Toronto, ON). The reaction products are electrophoretically separated and detected. The data is analyzed using GeneObjects software (Visible Genetics Inc., Toronto, ON) to base-call (i.e. determine the DNA sequence) of the samples. The base-called sequence is compared to the known *C. trachomatis* sequence to confirm diagnosis. Results are reported to the patient file.

EXAMPLE 2

The method of the invention may be employed to identify not only the presence of *C. trachomatis* in a patient sample but also the strain identity. Health care workers currently seek to distinguish among *Chlamydia trachomatis* strains to determine the molecular epidemiologic association of a range of diseases with infecting genotype (See Dean, D. et al "Major Outer Membrane Protein Variants of *Chlamydia trachomatis* Are Associated with Severe Upper Genital Tract Infections and Histopathology in San Francisco." *J. Infect. Dis.* 172: 1013–22 (1995)).

A suitable strain specific target for *C. trachomatis* is the omp1 (outer membrane protein) gene which has at least 4 variable sequence ("VS") domains that may be used to distinguish among the 15 known genotypes of *C. trachomatis* (Yuan, Y. et al. "Nucleotide and Deduced Amino Acid Sequences for the Four Variable Domains of the Major Outer Membrane Proteins of the 15 *Chlamydia trachomatis* Serovars" Infect. Immun. 57 1040–1049 (1989)).

Strain identification is achieved using the method of Example 1 with the following modifications. First of all, because of the length of the VS domains, separate reactions are performed to obtain sequence from VS1/VS2 and VS3/VS4. The following oligonucleotide primers may be employed:

| Name | Sequence | |
|---|---|---|
| For VS1/VS2: | | |
| MF21 | CCGACCGCGT CTTGAAAACA GATGT | [SEQ. ID NO. 3] |
| MB22 | CACCCACATT CCCAGAGAGC T | [SEQ. ID NO. 4] |
| For VS3/VS4 | | |
| MVF3 | CGTGCAGCTT TGTGGGAATG T | [SEQ. ID NO. 5] |
| MB4 | CTAGATTTCA TCTTGTTCAA TTGC | [SEQ. ID NO. 6] |

These sequencing primers were employed previously for PCR amplification reactions, but not sequencing. Mahoney et al., supra.

These oligonucleotide primers are used in separate reactions in place of KL1 and KL2 in Example 1. The sample preparation and sequencing reactions are performed as in Example 1. The reaction products are electrophoretically separated and detected on a MicroGene Blaster automated DNA sequencing apparatus (Visible Genetics Inc., Toronto, ON). The data is analyzed using GeneObjects software to base-call the samples and to compare the data to the known varieties of *C. trachomatis*. Pure populations generally give unambiguous sequence data. Where heterozygous mixed populations are detected, a circumstance thought to occur in 1–3% of clinical *C. trachomatis* samples, the software identifies the strains which could be combined to result in the particular heterozygote sample detected.

EXAMPLE 3

Strain-specific *C. trachomatis* identification over the VS1/VS2 domain can be achieved according to the method in Example 1, by using the following degenerate primers sets:

Forward
OMP291:    AGCATGCGTR TKGGTTACTA YGG   [SEQ ID NO. 7]
(labeled with Cy5.5). Base 175 to 197 of the ORF of the omp1
gene of C. trachomatis.
Forward
OMP314A:   TGACTTTGTT TTCGACCGYG TTTT   [SEQ ID NO. 8]
(labeled with Cy5.5). Base 198 to 221 of the ORF of the omp1
gene of C. trachomatis.
Reverse
OMP722:    CTAAAGTYGC RCATCCACAT TCC   [SEQ ID NO. 9]
Base 637 to 615 of the ORF of the omp1 (in serovar K) gene of C.
trachomatis. The primer may not have the EXACT SAME sequence as
in serovar K.
Reverse
OMP711:    CATCCACATT CCCASARAGC TGC   [SEQ ID NO. 10]
Base 626 to 604 of the ORF of the omp1 (in serovar K) gene of C.
trachomatis. The primer may not have the exact same sequence as
in serovar K.

These primers sets are preferably used in the following combinations:

(1) OMP291-OMP722, sequencing a 455 to 463-bp (depending on the serotype) fragment of the omp1 gene of C. trachomatis; or (2) OMP314A-OMP711, sequencing a 421 to 430-bp (depending on the serotype) fragment of the omp1 gene of C. trachomatis.

EXAMPLE 4

The method as exemplified in Examples 1, 2 and 3 may be further improved by employing different labels, preferably fluorescent labels, on the different primers for use in a multi-dye sequencer. This method takes advantage of the fact that a given termination mixture containing, for example, ddATP will give chain termination products for the A nucleotide in both directions. The different primer labels means that one reaction mixture loaded in a single lane of an automated DNA sequencing apparatus designed to detect the two labels (a "multi-dye sequencer") will identify the A nucleotide of both sense and antisense strands. Separate reactions are performed for the other 3 nucleotides. Using only 4 lanes of an electrophoresis gel, and 4 reaction mixtures, the DNA sequences of both the sense and antisense strands can be obtained. This information allows the operator to resolve any ambiguities that may be present.

Use of two different labels lends itself to a further improvement. As noted above, in a reaction according to the invention, the results of the ddATP reaction will give chain termination products for the A nucleotide in both directions. Since the A nucleotide in one direction corresponds to the T nucleotide in the other, a single reaction can provide the location of two bases. A second termination reaction with, for example, ddCTP will then obtain the positions of the other two nucleotides, C and G. Thus only two lanes of an electrophoresis gel and 2 reaction mixtures are required to identify the location of all 4 bases of the sequence.

A suitable multi-dye sequencer for use with this aspect of the invention, is the Applied Biosystems 377 Prism automated DNA sequencer (Applied Biosystems Inc., Foster City, Calif.). The fluorescent labels are selected to be detectable on the 377 instrument. Instead of the dye-terminator chemistry suggested in the Applied Biosystems product literature, however, the fluorescent labels must be conjugated to the 5' end of the primer molecules. The samples are electrophoresed, detected and the detected data is recorded.

Sophisticated software such as GeneObjects software (Visible Genetics Inc, Toronto, CA) may be used to assist in evaluation of the results. This software may employ the methods of commonly assigned U.S. patent applications Ser. Nos. 08/497,202 and 08/670,534 and International Patent Application No. PCT/US96/11130, all of which are incorporated herein by reference. In one of the methods, the single nucleotide data tracks are evaluated and nucleotides are positioned relative to the known (or standard) DNA sequence expected from the sample. When data tracks are generated for each of the four nucleotides, the full DNA sequence of the sample may be base-called. The base-called sequence is then compared to the library of known sequences to determine which C. trachomatis strain or strains are present in the sample.

EXAMPLE 5

The sequence of both the sense strand and antisense strand of a C. trachomatis cryptic plasmid gene may be obtained in a one step reaction using the primers:

| Name   | Sequence              |                |
|--------|-----------------------|----------------|
| KL1:   | TCCGGAGCGA GTTACGAAGA | [SEQ ID NO. 1] |
| CT1590:| ATGCCCGGGA TTGGTTGATC | [SEQ ID NO. 11]|

Combine the following materials and mix well:

|                                | Concentration | Amount   |
|--------------------------------|---------------|----------|
| Patient Sample DNA             |               | 11.25 ul |
| KL1*Cy5.5 Primer               | 10 uM         | 3 ul     |
| CT1590*Fluoresceine Primer     | 10 uM         | 2 ul     |
| Enzyme Diluent (Amersham plc)  |               | 8 ul     |
| ThermoSequenase Enzyme         | 32 U/ul       | 0.9 ul   |
| double distilled H$_2$O        |               | 24.2 ul  |

Take 11 ul of the mixture and add 2 ul of 13×buffer [Tris-HCl 260 mM pH 8.3, MgCl$_2$ 39 mM] (final concentration 20 mM Tris-HCl pH 8.3, 3 mM MgCl$_2$). Mix well and place 3 ul into each of 4 tubes. Heat tube to 94° C. for 5 mins then reduce temperature to 85° C. Add and mix 3 ul of an 85 C dNTP/ddNTP solution consisting of 0.75 mM each dNTP and 2.5 uM of a chain terminating nucleotide triphosphate (ddNTP) (use a different ddNTP in each of the 4 tubes).

Treat the mixture to 60 cycles of the following thermal cycling reactions: 94° C. for 10 sec, 62° C. for 15 sec, 70° C. for 1 min. Upon completion, treat the mixture for a final 5 min at 70° C. and then store at 4° C. until ready for loading. For viewing the reaction products, add an equal volume of stop/loading solution (95% formamide plus a colored dye). Take 1.5 ul and load in a single lane of a MicroGene Blaster automated DNA sequencer (Visible Genetics Inc., Toronto). Load the remaining mixture (@10.5 ul) in a single lane of an ALF Automated Sequencer (Pharmacia LKB, Uppsala, Sweden). The reaction products from the Cy5.5 labeled primer are detected on the MicroGene Blaster using GeneObjects Software. The reaction products from the fluorescein labeled primer are detected on the ALF Automated Sequencer using GeneObjects Software. The base-calling results of the Cy5.5 labeled primer were compared to the known sequence of the gene by the GeneLibrarian component of GeneObjects.

EXAMPLE 6

As described in U.S. patent application Ser. No. 08/577,858, not all 4 nucleotides of C. trachomatis, or any polymorphic or multiple allelic locus of any gene or organism necessarily need to be determined in order to ascertain which allele or variant is present. In many cases, positioning less than four nucleotides may be sufficient to determine with certainty which allele is present. The method of Examples 1–4 may be modified to obtain single nucleotide data tracks (or fragment patterns) by performing only one of the termination reactions at a time.

In the case of detection and serotyping of C. trachomatis, the evaluation of the A track alone over the first 100 nucleotides of the omp1 gene, aligning to nucleotides 249–349 of the serovars C and K, can distinguish the serovars. Appendix II is a text file representation of the omp1 gene in each of the serovars. The sequences are all aligned to the last (3') nucleotide of the detectably labeled primer omp314A. (Appendix II shows sequences starting 29 bp downstream of the 3'-nucleotide.) This illustration differs from a traditional "consensus" sequence illustrations in that all missing bases (usually represented by N's or raised dashes) are deleted. The A's are illustrated in the order and positions in which they would be expected to appear after a sequencing reaction and upon detection by an automated DNA electrophoresis apparatus.

If, in another microorganism, the A lane (or other preferred first lane) were not sufficient to distinguish all types, a second reaction for the C, G or T nucleotide could be performed to further define the qualitative nature of any target microorganism present in the sample. Because the sequences of the types are previously known, the operator can determine which of the nucleotides provide the greatest information and will analyze those nucleotides first.

EXAMPLE 7

The presence of and strain identity of C. trachomatis in a patient sample may be determined according to the methods of the previous examples by substituting the following primer pairs. These primers are used to determine the sequence of the omp1 gene (publicly available at DNASIS Accession No. X62921). Forward Primer (5' Primer) labeled with a detectable label such as Cy5.5:

Primer OMP312: GGAGACTTTG TTTTCGACCG [SEQ ID NO 12]
Position 312–331 of X62921 and one of the following Reverse Primers (3' Primer) (optionally labeled with a detectable label different from the 5' primer):

Primer OMP708: CATTCCCACA AAGCTGCGCG [SEQ ID NO 131
Position 727–708 of X62921
Primer OMP706: TTCCCACAAA GCTGCGCGAG [SEQ ID NO 14]
Position 725–706 of X62921
Primer OMP704: CCCACAAAGC TGCGCGAGCG [SEQ ID NO 15]
Position 723–704 of X62921

The following combination can be used to obtain DNA sequence over the following maximum lengths: OMP312-OMP708: 416-nt region of omp1 OMP312-OMP706: 414-nt region of omp1 OMP312-OMP704: 412-nt region of omp1

EXAMPLE 8

The presence of and strain identity of C. trachomatis in a patient sample may be determined according to the method of previous examples, using C. trachomatis ribosomal DNA (rDNA) specific primers such as CT220  ACCTTTCGGT TGAGGGAGAG TCTA  [SEQ ID NO 16]
and
CT447  GGACCAATTC TTATTCCCAA GCGA  [SEQ ID NO 17]

Haydock et al., Chap 1.10 in Persing et al., supra.

EXAMPLE 9

The sequence of both the sense strand and antisense strand of the protease gene of HIV-1 integrated into natural abundance DNA of lymphocytes may be obtained in a one step reaction as follows.

Natural abundance DNA is prepared from the patient blood lymphocyte sample according to a standard method such as a standard salting-out procedure (as provided by the Puregene DNA Isolation Kit, Gentra Systems, Inc., Minneapolis) or by detergent and proteinase K treatment (Current Protocols in Molecular Biology, Eds. Ausubel, F. M. et al, (John Wiley & Sons; 1995)).

Combine the following materials and mix well:

|  | Concentration | Amount |
| --- | --- | --- |
| Patient Sample DNA |  | 11.25 ul |
| PR211F*Cy5.5 Primer | 10 uM | 3 ul |
| or |  |  |
| PR281*Cy5.5 Primer | 10 uM | 3 ul |
| PR526*Fluorescein Primer | 10 uM | 2 ul |
| Enzyme Diluent (Amersham plc) |  | 8 ul |
| THERMOSEQUENASE Enzyme | 32 U/ul | 0.9 ul |
| double distilled H$_2$O |  | 24.2 ul |

The primers have the following sequences:

Name  Sequence

Choice of Forward Primers
PR211F  ATCACTCTTT GGCAACGACC  [SEQ ID No. 18] (FORWARD), BASE 6 TO 25 OF THE PROTEASE GENE
PR281   CAGGAGCAGA TGATACAGTA TTAG  [SEQ ID No. 19] (FORWARD), BASE 76 TO 99 OF THE PROTEASE GENE
Reverse Primer
PR526:  CCATTCGTGG CTTTAATTTT ACTGG  [SEQ ID No. 20] (REVERSE), BASES 321 TO 345 OF THE PROTEASE GENE PR211F-PR526 creates a sequencing fragment of maximum size 340 bp. PR281-PR526 creates a sequencing fragment of maximum size 270 bp. Both regions contain the sequence of the various codons where mutations are involved in protease inhibitor resistance (Codons 46, 48, 54, 63 82 84 and 90).

Take 11 ul of the mixture and add 2 ul of 13× buffer [Tris-HCl 260 mM pH 8.3, MgCl$_2$ 39 mM] (final concentration 20 mM Tris-HCl pH 8.3, 3 MM MgCl$_2$). Mix well and place 3 ul into each of 4 tubes. Heat tube to 94° C. for 5 mins then reduce temperature to 85° C. Add and mix 3 ul of an 85 C dNTP/ddNTP solution consisting of 0.75 mM each dNTP and 2.5 uM of a chain terminating nucleotide triphosphate (ddNTP) (use a different ddNTP in each of the 4 tubes).

Treat the mixture to 60 cycles of the following thermal cycling reactions: 94 C. for 10 sec, 62 C. for 15 sec, 70 C. for 1 min. Upon completion, treat the mixture for a final 5 min at 70 C. and then store at 4 C. until ready for loading. For viewing the reaction products, add an equal volume of stop/loading solution (95% formamide plus a coloured dye).

Take 1.5 ul and load in a single lane of a MicroGene Blaster automated DNA sequencer (Visible Genetics Inc., Toronto). Load the remaining mixture (@ 10.5 ul) in a single lane of an ALF Automated Sequencer (Pharmacia LKB, Uppsala, Sweden). The reaction products from the Cy5.5 labelled primer are detected on the MicroGene Blaster using GeneObjects Software. The reaction products from the fluorescein labeled primer are detected on the ALF Automated Sequencer using GeneObjects Software. The base-called results from each primer were compared to the known sequences of HIV-1 by GeneLibrarian (a component of GeneObjects (Visible Genetics Inc, Toronto).

EXAMPLE 10

The presence and type of human papilloma virus (HPV) present in a patient sample can be determined according to the method of the invention by following the protocol in Example 1 with the following modifications.

Patient sample DNA is extracted from 250 ul urine specimens using Geneclean II (Bio 101, Inc.). The sample is then treated as described previously but employing the degenerate primer pair:

| | |
|---|---|
| Forward Primer: MY11 | |
| GCMCAGGGWC ATAAYAATGG | [SEQ ID No. 21] |
| Reverse Primer: MY09 | |
| CGTCCMAARG GAWACTGATC | [SEQ ID NO. 22) |

The reactions are performed as before, using ThermoSequenase enzyme or the like. Reaction products are detected on an automated electrophoresis/detection device such as the MicroGene Blaster. The sequence is analyzed and compared to the known varieties of HPV to identify the type. The result is reported to the patient file.

APPENDIX I

Suitable Sequencing Primer Pairs for Identification and
Sub-Typing of Infectious Pathogens
cf. Diagnostic Molecular Microbiology (Eds. Persing et al.)
(1993; American Society for Microbiology; Washington D.C.)

Bacterial Pathogens Universal (16S rDNA) Typing Primers

Pathogen Name: Universal Bacterial Identification
Gene: 16s rDNA
Forward Primer: 91E
TCAAAKGAAT TGACGGGGGC                          [SEQ ID No. 23]
Site of Specific Hybridization: nt 911–930
Reverse Primer: 13B
AGGCCCGGGA ACGTATTCAC                          [SEQ ID No. 24]
Site of Specific Hybridization: nt 1390–1371
Maximum fragment size: 475 nt
Pathogen Name: Universal Bacterial Identification
Gene: 16s rDNA
Forward Primer: 515FPL
TGCCAGCAGC CGCGGTAA                            [SEQ ID No. 25]
Site of Specific Hybridization: nt 515–533
Reverse Primer: 806R
GGACTACCAG GGTATCTAAT                          [SEQ ID No. 26]
Site of Specific Hybridization: nt 806–787
Maximum fragment size: 328 nt
Pathogen Name: Universal Bacterial Identification
Gene: 16s rDNA
Forward Primer: 11E
GAGGAAGGTG GGGATGACGT                          [SEQ ID No. 27]
Site of Specific Hybridization: nt 1175–1194
Reverse Primer: 13B
AGGCCCGGGA ACGTATTCAC                          [SEQ ID No. 28]
Site of Specific Hybridization: nt 1390-1371
Maximum fragment size: 233 nt
Pathogen Name: Eubacterial Typing (Broad range of eubacteria)
Gene: 16S rDNA
Forward Primer: 285
GAGAGTTTGA TCCTGGCTCA G                        [SEQ ID No. 29]
Site of Specific Hybridization: nt 9–30
Reverse Primer: 244
CCCACTGCTG CCTCCCGTAG                          [SEQ ID No. 30]
Site of Specific Hybridization: nt 341–361
Maximum fragment size: 352 bp
Bacteria Pathogen Name: Mycobacteria Typing (*M. tuberculosis* complex)
Gene: 16S rDNA
Forward Primer: 285
GAGAGTTTGA TCCTGGCTCA G                        [SEQ ID No. 31]
Site of Specific Hybridization: nt 9–30
Reverse Primer: 259
TTTCACGAAC AACGCGACAA                          [SEQ ID No. 32]
Site of Specific Hybridization: nt 590–609
Maximum fragment size: 600 bp
Pathogen Name: *Mycobacterium tuberculosis*

APPENDIX I-continued

Suitable Sequencing Primer Pairs for Identification and
Sub-Typing of Infectious Pathogens
cf. Diagnostic Molecular Microbiology (Eds. Persing et al.)
(1993; American Society for Microbiology; Washington D.C.)

Gene: IS6110
Forward Primer: T5
CTCGTCCAGC GCCGCTTCGG   [SEQ ID No. 33]
Site of Specific Hybridization: nt 758–788
Reverse Primer: T4
CCTGCGAGCG TAGGCGTCGG   [SEQ ID No. 34]
Site of Specific Hybridization: nt 881–862
Maximum fragment size: 123 bp
Pathogen Name: *Rickettsia rickettsii* (Rocky Mountain spotted fever)
Gene: 17 K Da Ag Gene
Forward Primer: TZ15
TTCTCAATTC GGTAAGGC   [SEQ ID No. 35]
Site of Specific Hybridization: nt 191–209
Reverse Primer: TZ16
ATATTGACCA GTGCTATTTC   [SEQ ID No. 36]
Site of Specific Hybridization: nt 437–419
Maximum fragment size: 247 bp
Pathogen Name: *Ehrlichia chaffeensis*
Gene: 16s rDNA
Forward Primer: HE1
CAATTGCTTA TAACCTTTTG GTTATAAAT   [SEQ ID No. 37]
Site of Specific Hybridization: nt 49–77
Reverse Primer: HE3
TATAGGTACC GTCATTATCT TCCCTAT   [SEQ ID No. 38]
Site of Specific Hybridization: nt 438–412
Maximum fragment size: 390 bp
Pathogen Name: *Borrelia burgdorferi* (Lyme disease)
Gene: Outer Surface Protein A
Forward Primer: OSPA149
TTATGAAAAA ATATTTATTG GGAAT   [SEQ ID No. 39]
Site of Specific Hybridization: nt 1
Reverse Primer: OSPA319
CTTTAAGCTC AAGCTTGTCT ACTGT   [SEQ ID No. 40]
Site of Specific Hybridization: nt 193
Maximum fragment size: 193 bp
Pathogen Name: *Borrelia burgdorferi* (Lyme disease)
Gene: Outer Surface Protein A
Forward Primer: OSPA4
CTGCAGCTTG GAATTCAGGC ACTTC   [SEQ ID No. 41]
Site of Specific Hybridization: nt 638
Reverse Primer: OSPA2
GTTTTGTAAT TTCAACTGCT GACC   [SEQ ID No. 42]
Site of Specific Hybridization: nt 793
Maximum fragment size: 156 bp
Pathogen Name: *Borrelia burgdorferi* (Lyme disease)
Gene: 16s rDNA
Forward Primer: DD06
ATCTGTTACC AGCATGTAAT   [SEQ ID NO. 43]
Site of Specific Hybridization: nt 1105
Reverse Primer: DD02
CCCTCACTAA ACATACCT   [SEQ ID No. 44]
Site of Specific Hybridization: nt 1472
Maximum fragment size: 368 bp
Pathogen Name: *Borrelia burgdorferi* (Lyme disease)
Gene: Flagellin
Forward Primer: FLA1
GATGATGCTG CTGGCATGGG AGTTTCTGG   [SEQ ID No. 45]
Site of Specific Hybridization: nt 121
Reverse Primer: FLA3
CTGTCTGCAT CTGAATATGT GCCGTTACCT G   [SEQ ID No. 46]
Site of Specific Hybridization: nt 320
Maximum fragment size: bp
Pathogen Name: *Yersinia pestis* (the bubonic plague)
Gene: 9.5 kb pesticin plasmid
Forward Primer: Yp1
ATCTTACTTT CCGTGAGAAG   [SEQ ID No. 47]
Site of Specific Hybridization: nt 971–990
Reverse Primer: Yp2
CTTGGATGTT GAGCTTCCTA   [SEQ ID No. 48]
Site of Specific Hybridization: nt 1450–1431
Maximum fragment size: 478 bp
Pathogen Name: *Treponema pallidum* (venereal syphilis)
Gene: 47-kDA gene

APPENDIX I-continued

Suitable Sequencing Primer Pairs for Identification and
Sub-Typing of Infectious Pathogens
cf. Diagnostic Molecular Microbiology (Eds. Persing et al.)
(1993; American Society for Microbiology; Washington D.C.)

Forward Primer: 47-3
TTGTGGTAGA CACGGTGGGT AC  [SEQ ID No. 49]
Site of Specific Hybridization: nt 692–713
Reverse Primer: 47-4
TGATCGCTGA CAAGCTTAGG CT  [SEQ ID No. 50]
Site of Specific Hybridization: nt 1187–1166
Maximum fragment size: 496 bp
Pathogen Name: *Treponema pallidum* (venereal syphilis)
Gene: 16S rDNA
Forward Primer: Tpr3
CTCAGAGATG AGCCTGCGAC CATT  [SEQ ID NO. 51]
Site of Specific Hybridization: nt 230
Reverse Primer: TPr4
GCATTCCCTC CCGTCCTCAT TCTTC  [SEQ ID No. 52]
Site of Specific Hybridization: nt 480
Maximum fragment size: 251 bp
Pathogen Name: *Chlamydia trachomatis* (infection of mucosal surfaces)
Gene: MOMP
Forward Primer: CT.0005
GATAGCGAGC ACAAAGAGAG CTAA  [SEQ ID No. 53]
Site of Specific Hybridization: nt 67
Reverse Primer: CT.06
TTCACATCTG TTTGCAAAAC ACGGTCGAAA ACAAAG  [SEQ ID No. 54]
Site of Specific Hybridization: nt 347
Maximum fragment size: 281 bp
Pathogen Name: *Chlamydia pneumoniae* (respiratory disease)
Gene: 474bp PST fragment
Forward Primer: HL-1
GTTGTTCATG AAGGCCTACT  [SEQ ID No. 55]
Site of Specific Hybridization: nt 30–49
Reverse Primer: HR-1
TGCATAACCT ACGGTGTGTT  [SEQ ID No. 56]
Site of Specific Hybridization: nt 467–448
Maximum fragment size: 438 bp
Pathogen Name: *Mycoplasma pneumoniae* (respiratory disease)
Gene: genomic
Forward Primer: MP5-1
GAAGCTTATG GTACAGGTTG G  [SEQ ID No. 57]
Reverse Primer: MP5-2
ATTACCATCC TTGTTGTAAG  [SEQ ID No. 58]
Maximum fragment size: 144 bp
Pathogen Name: *Mycoplasma speciation* (Universal Primers for 8 most common Mycoplasma species)
Gene: 16S rDNA
Forward Primer: Primer A
GGCGAATGGG TGAGTAACAC G  [SEQ ID No. 59]
Site of Specific Hybridization: nt 87
Reverse Primer: Primer B
CGGATAACGC TTGCGACCTA TG  [SEQ ID No. 60]
Site of Specific Hybridization: nt 550
Maximum fragment size: 464 bp
Pathogen Name: *Legionella pneumophila* (wound infection, respiratory disease)
Gene:
Forward Primer: LEG1
GCTATGAGGA ATCTCGCTG  [SEQ ID No. 61]
Reverse Primer: LEG2
CTGGCTTCTT CCAGCTTCA  [SEQ ID No. 62]
Maximum fragment size: 800 bp
Pathogen Name: *Legionella dumoffii* (wound infection, respiratory disease)
Gene:
Forward Primer: LDBKS1
ATACACGTGG TGGAGGTAC  [SEQ ID No. 63]
Reverse Primer: LDBKS2
GCGGGCAATA TCTTGCATC  [SEQ ID No. 64]
Maximum fragment size: 1000 bp
Pathogen Name: *Mycoplasma fermentans*
Gene: IS-like element
Forward Primer: RW005
GGTTATTCGA TTTCTAAATC GCCT  [SEQ ID No. 65]
Site of Specific Hybridization: nt 1116
Reverse Primer: RW004

APPENDIX I-continued

Suitable Sequencing Primer Pairs for Identification and
Sub-Typing of Infectious Pathogens
cf. Diagnostic Molecular Microbiology (Eds. Persing et al.)
(1993; American Society for Microbiology; Washington D.C.)

GGACTATTGT CTAAACAATT TCCC [SEQ ID No. 66]
Site of Specific Hybridization: nt 1321
Maximum fragment size: 206 nt
Pathogen Name: Ehrlichia
Gene: 16S rDNA
Forward Primer: 8F
AGTTTGATCA TGGCTCAG [SEQ ID No. 67]
Site of Specific Hybridization: nt 32
Reverse Primer: GA1UR
GAGTTTGCCG GGACTTCTTC T [SEQ ID No. 68]
Site of Specific Hybridization: nt (about 400)
Maximum fragment size: (about 400 nt)
Viruses Human Immunodeficiency Virus Type 1 (HIV-1)
Gene: gag
Forward Primer: SK462
AGTTGGAGGA CATCAAGCAG CCATGCAAAT [SEQ ID No. 69]
Site of Specific Hybridization 1366–1395: nt
Reverse Primer: SK431
TGCTATGTCA GTTCCCCTTG GTTCTCT [SEQ ID No. 70]
Site of Specific Hybridization: nt 1507–1481
Maximum fragment size: 142 nt
Human T-Cell Lymphotrophic Virus Type 1 (HTLV-1)
Gene: POL
Forward Primer: POL1
CCCGGGCCCC CTGACTTGTC [SEQ ID No. 71]
Site of Specific Hybridization: nt 2802–2821
Reverse Primer: POL3
GCTTTCACTG TCCCACAGCAG [SEQ ID No. 72]
Site of Specific Hybridization: nt 2916–2936
Maximum fragment size: 237 nt
Hepatitis B Virus (HBV)
Gene: surface antigen
Forward Primer: Primer 1
CAAGGTATGT TGCCCGTTTG [SEQ ID No. 73]
Site of Specific Hybridization: nt 329–348
Reverse Primer: Primer 2
AAAGCCCTGC GAACCACTGA [SEQ ID No. 74]
Site of Specific Hybridization: nt 587–568
Maximum fragment size: 259 nt
Hepatitis C Virus (HCV)
Gene: 5'UT
Forward Primer: 5PUT c1-a
CCCAACACTA CTCGGCTAG [SEQ ID No. 75]
Site of Specific Hybridization: nt −74—92
Reverse Primer: 5PUT 1-s
AACTACTGTC TTCACGCAGA AAGC [SEQ ID No. 76]
Site of Specific Hybridization: nt −266—289
Maximum fragment size: 216 nt
Herpes simplex virus (HSV)
Gene: DNA polymerase gene
Forward Primer: HSV-3
TACATCGGCG TCATCTGCGG GG [SEQ ID No. 77]
Site of Specific Hybridization: nt 2821–2842
Reverse Primer: HSV-4
CAGTTCGGCG GTGAGGACAA AG [SEQ ID No. 78]
Site of Specific Hybridization: nt 3090–3111
Maximum fragment size: 290 nt
Herpesvirus 6
Gene:
Forward Primer: H6-6
AAGCTTGCAC AATGCCAAAA AACAG [SEQ ID No. 79]
Reverse Primer: H6-7
CTCGAGTATG CCGAGACCCC TAATC [SEQ ID No. 80]
Maximum fragment size: 223 nt
Herpesvirus 7
Gene:
Forward Primer: HV7
TATCCGAGCT GTTTTCATAT AGTAAC [SEQ ID No. 81]
Reverse Primer: HV8
GCCTTGCGGT AGCACTAGAT TTTTTG [SEQ ID No. 82]
Maximum fragment size: 186 nt
Epstein-Barr Virus

APPENDIX I-continued

Suitable Sequencing Primer Pairs for Identification and
Sub-Typing of Infectious Pathogens
cf. Diagnostic Molecular Microbiology (Eds. Persing et al.)
(1993; American Society for Microbiology; Washington D.C.)

Gene: EBNA2
Forward Primer: E2p1
AAGGATGCCT GGACACAAGA [SEQ ID No. 83]
Site of Specific Hybridization: nt 1813–1833
Reverse Primer: E2p2
TGGTGCTGCT GGTGGTGGCA AT [SEQ ID No. 84]
Site of Specific Hybridization: nt 2409–2388
Maximum fragment size: 596 nt
Cytomegalovirus (CMV) (member of Herpesviridae)
Gene: CMV IE gene
Forward Primer: CMV1
CCTAGTGTGG ATGACCTACG GGCCA [SEQ ID No. 85]
Site of Specific Hybridization: nt 1234–1258
Reverse Primer: CMV2
CAGACACAGT GTCCTCCCGC TCCTC [SEQ ID No. 86]
Site of Specific Hybridization: nt 1459–1483
Maximum fragment size: 249 nt
Varicella-Zoster Virus (VZV) (for Chicken Pox)
Gene: unique genomic fragment
Forward Primer: VZ7
ATGTCCGTAC AACATCAACT [SEQ ID No. 87]
Site of Specific Hybridization: nt 3377–3396
Reverse Primer: VZ8
CGATTTTCCA AGAGAGACGC [SEQ ID No. 88]
Site of Specific Hybridization: nt 3643–3624
Maximum fragment size: 267 nt
JC Virus (JCV) distinguishing from BK virus and simian virus 40
Gene: T antigen
Forward Primer: P5
AGTCTTTAGG GTCTTCTACC [SEQ ID No. 89]
Site of Specific Hybridization: nt 4255–4274
Reverse Primer: P6
GGTGCCAACC TATGGAACAG [SEQ ID No. 90]
Site of Specific Hybridization: nt 4427–4408
Maximum fragment size: 172 nt
Parvovirus B19
Gene: VP Protein
Forward Primer: Z
GGAACAGACT TAGAGCTTAT TC [SEQ ID No. 91]
Site of Specific Hybridization: nt 2537
Reverse Primer: Y
GCTTGTGTAA GTCTTCACTA G [SEQ ID No. 92]
Site of Specific Hybridization: nt 2774
Maximum fragment size: 259 nt
Influenza A (Orthomyxoviridae)
Gene: hemagglutinin H2
Forward Primer: AH2B
CAATAGCTGG TTTTATAGAA [SEQ ID No. 93]
Site of Specific Hybridization: nt 1077
Reverse Primer: AH2CII
TTATCATACA GATTCTTGAC [SEQ ID No. 94]
Site of Specific Hybridization: nt 1425
Maximum fragment size: 349 nt
Influenza B (Orthomyxoviridae)
Gene: Matrix Protein
Forward Primer: BMPB
GAAGGCAAAG CAGAACTAGC [SEQ ID No. 95]
Site of Specific Hybridization: nt 79
Reverse Primer: BMPCII
TGGCCTTCTG CTATTTCAAA [SEQ ID No. 96]
Site of Specific Hybridization: nt 380
Maximum fragment size: 302 nt
Influenza C (Orthomyxoviridae)
Gene: hemagglutinin
Forward Primer: CHAB
GTGCAAACTG CATCTTGTGG [SEQ ID No. 97]
Site of Specific Hybridization: nt 705
Reverse Primer: CHACII
CTCATTTCTT GATCTCCATG [SEQ ID No. 98]
Site of Specific Hybridization: nt 1145
Maximum fragment size: 441 nt
Rotavirus
Gene: vp7
Forward Primer: A2

APPENDIX I-continued

Suitable Sequencing Primer Pairs for Identification and
Sub-Typing of Infectious Pathogens
cf. Diagnostic Molecular Microbiology (Eds. Persing et al.)
(1993; American Society for Microbiology; Washington D.C.)

GGACCAAGAG AAAACGTAGC [SEQ ID No. 99]
Site of Specific Hybridization: nt 805
Reverse Primer: A4
GGTCACATCA TACAATTCTA ATCTAAG [SEQ ID No. 100]
Site of Specific Hybridization: nt 1062
Maximum fragment size: 257 nt
Human Adenovirus
Gene: Hexon gene
Forward Primer: A2H/pcr 4R
ATGACTTTTG AGGTGGATCC CATGGA [SEQ ID No. 101]
Reverse Primer: A2H/pcr 1
GCCGAGAAGG GCGTGCGCAG GTA [SEQ ID No. 102]
Maximum fragment size: 134 nt
Rubella Virus
Gene: 40S ssRNA
Forward Primer: Ru2
TGCTTTGCCC CATGGGACCT CGAG [SEQ ID No. 103]
Site of Specific Hybridization: nt 1990–2013
Reverse Primer: Ru3
GGCGAACACG CTCATCACGG T [SEQ ID No. 104]
Site of Specific Hybridization: nt 2310–2290
Maximum fragment size: 321 nt
Human Enteroviruses
Gene: 5'NTR
Forward Primer: MD91
CCTCCGGCCC CTGAATGCGG CTAAT [SEQ ID No. 105]
Site of Specific Hybridization: nt 444–468
Reverse Primer: MD90
ATTGTCACCA TAAGCAGCCA [SEQ ID No. 106]
Site of Specific Hybridization: nt 577–596
Maximum fragment size: 154 nt
Genital Human Papillomavirus (HPV)
Gene: L1 gene
Forward Primer: MY11
GCMCAGGGWC ATAAYAATGG [SEQ ID No. 107]
Site of Specific Hybridization: nt 6582
Reverse Primer: MY09
CGTCCMAARG GAWACTGATC [SEQ ID No. 108]
Site of Specific Hybridization: nt 7033
Maximum fragment size: 450 nt
Hantavirus
Gene: M segment
Forward Primer: Har M 30+
CACTGAATAA GAGGATACAA GAATGG [SEQ ID No. 109]
Site of Specific Hybridization: nt 30
Reverse Primer: Har M 403−
GGAGGAATAT TACATGTGCC TTT [SEQ ID No. 110]
Site of Specific Hybridization: nt 403
Maximum fragment size: 374 nt
Fungi

*Cryptococcus neoformans* (Universal fungal primers)
Gene:
Forward Primer: ITS1
TCCGTAGGTG AACCTGCGA [SEQ ID No. 111]
Reverse Primer: ITS4
TCCTCCGCTT ATTGATATGC [SEQ ID No. 112]
Maximum fragment size: 600 nt
*Pneumocystis carinii*
Gene: 5S rDNA
Forward Primer: 5S Sense
AGTTACGGCC ATACCTCAGA [SEQ ID No. 113]
Reverse Primer: 5S Antisense
AAAGCTACAG CACGTCGTAT [SEQ ID No. 114]
Maximum fragment size: 120 nt
Fungal Pathogens (*Histoplasma capsulatum, Blastomyces dermatitidis, Coccidioides immitis Trichophyton rubrum*)
Gene: 18S rDNA
Forward Primer: NS3
GCAAGTCTGG TGCCAGCAGC C [SEQ ID No. 115]
Site of Specific Hybridization: nt 551
Reverse Primer: RDR116
CCGTCAATTC CTTTATGTTT CAGCCTT [SEQ ID No. 116]
Site of Specific Hybridization: nt 1149

APPENDIX I-continued

Suitable Sequencing Primer Pairs for Identification and
Sub-Typing of Infectious Pathogens
cf. Diagnostic Molecular Microbiology (Eds. Persing et al.)
(1993; American Society for Microbiology; Washington D.C.)

Maximum fragment size: 599 nt
Protozoa

*Trypanosoma cruzi*
Gene: kinetoplase
Forward Primer: S35
AAATAATGKA CGGGTGAGAT GCATGA          [SEQ ID No. 117]
Reverse Primer: S36
GGGTTCGATT GGGGTTGGTG T               [SEQ ID No. 118]
Maximum fragment size: 330 nt
Leishmania species
Gene: kinetoplast
Forward Primer: 13A
GTGGGGGAGG GGCGTTCT                   [SEQ ID No. 119]
Reverse Primer: 13B
ATTTTACACC AACCCCCAGT T               [SEQ ID No. 120]
Maximum fragment size: 120 nt
Plasmodium (genus specific)
Gene: Nuclear small subunit rDNA
Forward Primer: 566R
GGATAACTAC GGAAAAGCTG TAGC            [SEQ ID No. 121]
or Forward Primer: 570R
CGACTTCTCC TTCCTTTAAA AGATAGG         [SEQ ID No. 122]
Reverse Primer: 567R
GTTCAAGATT AATAATTGCA ATAATCTATC CC   [SEQ ID No. 123]
Maximum fragment size: about 500 nt
*Entamoeba histolytica* (amoebic dysentery)
Gene: SSU rDNA
Forward Primer: Psp5
GGCCAATTCA TTCAATGAAT TGAG            [SEQ ID No. 124]
Site of Specific Hybridization: nt 200
Reverse Primer: Psp3
CTCAGATCTA GAAACAATGC TTCTC           [SEQ ID No. 125]
Site of Specific Hybridization: nt 1075
Maximum fragment size: 876 nt
*Babesia microti*
Gene: SS rDNA
Forward Primer: Bab1
CTTAGTATAA GCTTTTATAC AGC             [SEQ ID No. 126]
Site of Specific Hybridization: nt 38–60
Reverse Primer: Bab4
ATAGGTCAGA AACTTGAATG ATACA           [SEQ ID No. 127]
Site of Specific Hybridization: nt 251–275
Maximum fragment size: 238 nt
*Giardia lamblia*
Gene: 18S rDNA gene
Forward Primer: JW1
GCGCACCAGG AATGTCTTGT                 [SEQ ID No. 128]
Site of Specific Hybridization: nt 1251–1270
Reverse Primer: JW2
TCACCTACGG ATACCTTGTT                 [SEQ ID No. 129]
Site of Specific Hybridization: nt 1433–1414
Maximum fragment size: 183 nt
Pathogen Name: *Cryptosporidium oocyst* detection
Gene: 18S rDNA
Forward Primer: CP1
CCGAGTTTGA TCCAAAAAGT TACGAA          [SEQ ID No. 130]
Reverse Primer: CP2
TAGCTCCTCA TATGCCTTAT TGAGTA          [SEQ ID No. 131]
Maximum fragment size: 452 nt
Pathogen Name: Cyclospora and Eimeria species
Gene: 18S rDNA
Forward Primer: CYC3FE
GGAATTCCTT CCGAGCTTCG CTGCGT          [SEQ ID No. 132]
Site of Specific Hybridization: nt 685–704
Reverse Primer: CYC4RB
CGGGATCCCG TCTTCAAACC CCCTACTG        [SEQ ID No. 133]
Site of Specific Hybridization: nt 978–959
Maximum fragment size: 294 nt
Identification of Bacterial Toxin Genes Pathogen Name: *Vibrio cholerae* 01 containing cholera toxin gene
(epidemic chloera)
Gene: CTXA

APPENDIX I-continued

Suitable Sequencing Primer Pairs for Identification and
Sub-Typing of Infectious Pathogens
cf. Diagnostic Molecular Microbiology (Eds. Persing et al.)
(1993; American Society for Microbiology; Washington D.C.)

Forward Primer: CTX2
CGGGCAGATT CTAGACCTCC TG                        [SEQ ID No. 134]
Site of Specific Hybridization: nt 73–94
Reverse Primer: CTX3
CGATGATCTT GGAGCATTCC CAC                       [SEQ ID No. 135]
Site of Specific Hybridization: nt 614–636
Maximum fragment size: 564 bp
Pathogen Name: Enterotoxigenic *Escherichia coli*
Gene: ST1a or ST1b
Forward Primer: ST1-1
TTAATAGCAC CCGGTACAAG CAGG [SEQ ID No. 189]
Site of Specific Hybridization: nt 243–266
Reverse Primer: ST1-2
CTTGACTCTT CAAAAGAGAA AATTAC                    [SEQ ID No. 136]
Site of Specific Hybridization: nt 127–144
Maximum fragment size: 147 bp
Pathogen Name: Enterotoxigenic *Escherichia coli*
Gene: LT1a or LT1b
Forward Primer: LT1a/b-1
TCTCTATRTG CAYACGGAGC                           [SEQ ID No. 137]
Site of Specific Hybridization: nt 46–65
Reverse Primer: LT1-2
CCATACTGAT TGCCGCAAT                            [SEQ ID No. 138]
Site of Specific Hybridization: nt 349–367
Maximum fragment size: 322 bp
Pathogen Name: Enterotoxigenic *Escherichia coli*
Gene: SLTII
Forward Primer: SLTII-1
CTTCGGTATC CTATTCCCGG                           [SEQ ID No. 139]
Site of Specific Hybridization: nt 288–307
Reverse Primer: SLTII-2
GGATGCATCT CTGGTCATTG                           [SEQ ID No. 140]
Site of Specific Hybridization: nt 747–766
Maximum fragment size: 478 bp
Pathogen Name: Shigella species and enteroinvasive *E. coli*
(diarrheal disease)
Gene: Invasion plasmid ial locus
Forward Primer: Sh-1
CTGGATGGTA TGGTGAGG                             [SEQ ID No. 141]
Reverse Primer: Sh-2
GGAGGCCAAC AATTATTTCC                           [SEQ ID No. 142]
Maximum fragment size: 320 bp
Pathogen Name: *Helicobacter pylori* (formerly *Campylobacter
pylori*)
Gene: genomic
Forward Primer: CAM-2
TAACAAACCG ATAATGGCGC                           [SEQ ID No. 143]
Reverse Primer: CAM-4
CATCTTGTTA GAGGGATTGG                           [SEQ ID No. 144]
Maximum fragment size: 203 bp
Pathogen Name: Toxigenic *Clostridium difficile*
Gene: rDNA
Forward Primer: PG-48
CTCTTGAAAC TGGGAGACTT GA                        [SEQ ID No. 145]
Reverse Primer: B
CCGTCAATTC MTTTRAGTTT                           [SEQ ID No. 146]
Maximum fragment size: 291 bp
Pathogen Name: Toxigenic *Clostridium difficile*
Gene: Toxin B
Forward Primer: YT-17
GGTGGAGCTT CAATTGGAGA G                         [SEQ ID No. 147]
Reverse Primer: YT-18
GTGTAACCTA CTTTCATAAC ACCAG                     [SEQ ID No. 148]
Maximum fragment size: 399 bp
Pathogen Name: *Staphylococcus aureus* toxins and virulence factors
Gene: sea
Forward Primer: SEA1
TTGGAAACGG TTAAAACGAA                           [SEQ ID No. 149]
Site of Specific Hybridization: nt 490–509
Reverse Primer: SEA2
GAACCTTCCC ATCAAAAACA                           [SEQ ID No. 150]
Site of Specific Hybridization: nt 610–591
Maximum fragment size: 120 bp
Pathogen Name: *Staphylococcus aureus* toxins and virulence factors

APPENDIX I-continued

Suitable Sequencing Primer Pairs for Identification and
Sub-Typing of Infectious Pathogens
cf. Diagnostic Molecular Microbiology (Eds. Persing et al.)
(1993; American Society for Microbiology; Washington D.C.)

Gene: seb
Forward Primer: SEB1
TCGCATCAAA CTGACAAACG                         [SEQ ID No. 151]
Site of Specific Hybridization: nt 634–653
Reverse Primer: SEB2
GCAGGTACTC TATAAGTGCC                         [SEQ ID No. 152]
Site of Specific Hybridization: nt 1110–1091
Maximum fragment size: 478 bp
Pathogen Name: *Staphylococcus aureus* toxins and virulence factors
Gene: sec
Forward Primer: SEC1
GACATAAAAG CTAGGAATTT                         [SEQ ID No. 153]
Site of Specific Hybridization: nt 676–695
Reverse Primer: SEC2
AAATCGGATT AACATTATCC                         [SEQ ID No. 154]
Site of Specific Hybridization: nt 932–913
Maximum fragment size: 257 bp
Pathogen Name: *Staphylococcus aureus* toxins and virulence factors
Gene: sed
Forward Primer: SED1
CTAGTTTGGT AATATCTCCT                         [SEQ ID No. 155]
Site of Specific Hybridization: nt 354–373
Reverse Primer: SED2
TAATGCTATA TCTTATAGGG                         [SEQ ID No. 156]
Site of Specific Hybridization: nt 671–652
Maximum fragment size: 317 bp
Pathogen Name: *Staphylococcus aureus* toxins and virulence factors
Gene: see
Forward Primer: SEE1
TAGATAAAGT TAAAACAAGC                         [SEQ ID No. 157]
Site of Specific Hybridization: nt 491–510
Reverse Primer: SEE2
TAACTTACCG TGGACCCTTC                         [SEQ ID No. 158]
Site of Specific Hybridization: nt 659–640
Maximum fragment size: 170 bp
Pathogen Name: *Staphylococcus aureus* toxins and virulence factors
Gene: tss
Forward Primer: TSST1
ATGGCAGCAT CAGCTTGATA                         [SEQ ID No. 159]
Site of Specific Hybridization: nt 251–270
Reverse Primer: TSST2
TTTCCAATAA CCACCCGTTT                         [SEQ ID No. 160]
Site of Specific Hybridization: nt 600–581
Maximum fragment size: 350 bp
Pathogen Name: *Staphylococcus aureus* toxins and virulence factors
Gene: eta
Forward Primer: ETA1
CTAGTGCATT TGTTATTCAA                         [SEQ ID No. 161]
Site of Specific Hybridization: nt 374–393
Reverse Primer: ETA2
TGCATTGACA CCATAGTACT                         [SEQ ID No. 162]
Site of Specific Hybridization: nt 492–473
Maximum fragment size: 119 bp
Pathogen Name: *Staphylococcus aureus* toxins and virulence factors
Gene: etb
Forward Primer: ETB1
ACGGCTATAT ACATTCAATT                         [SEQ ID No. 163]
Site of Specific Hybridization: nt 51–70
Reverse Primer: ETB2
TCCATCGATA ATATACCTAA                         [SEQ ID No. 164]
Site of Specific Hybridization: nt 250–231
Maximum fragment size: 200 bp
Pathogen Name: Bacterial meningitis (*Haemophilus influenzae*,
*Neisseria meningitidis*, *Streptococcus pneumonia*, *S. agalactiae*,
*Listeria monocytogenes*, enteric bacteria, or *Mycobacterium
tuberculosis*)
Gene: 16s rDNA
Forward Primer: RW01
AACTGGAGGA AGGTGGGGAT                         [SEQ ID No. 165]
Reverse Primer: DG74
AGGAGGTGAT CCAACCGCA                          [SEQ ID No. 166]
Maximum fragment size: 370 nt
Pathogen Name: *Streptococcus pyogenes* exotoxins (Streptococcal
Toxic Shock Syndrome)

APPENDIX I-continued

Suitable Sequencing Primer Pairs for Identification and
Sub-Typing of Infectious Pathogens
cf. Diagnostic Molecular Microbiology (Eds. Persing et al.)
(1993; American Society for Microbiology; Washington D.C.)

Gene: speC
Forward Primer: F
CCACCTTGAC TATTT                              [SEQ ID No. 167]
Reverse Primer: R
TTAATTAGGA GGTAA                              [SEQ ID No. 168]
Maximum fragment size: 936 nt
Identification of Anti-Microbial Resistance Loci Pathogen Name: Rifampin Resistance Mutations in *Mycobacterium
tuberculosis* and *M. leprae*
Gene: rpoB
Forward Primer: rpoB105
CGTGGAGGCG ATCACACCGC AGACGT                  [SEQ ID No. 169]
Reverse Primer: rpoB293
AGTGCGACGG GTGCACGTCG CGGACCT                 [SEQ ID No. 170]
Maximum fragment size: 215 nt
Pathogen Name: Human Immunodeficiency Virus Drug Resistance
Gene: HIV Reverse Transcriptase
Forward Primer: A(35)
TTGGTTGCAC TTTAAATTTT CCCATTAGTC CTATT         [SEQ ID No. 171]
Reverse Primer: NE-1(35)
CCTACTAACT TCTGTATGTC ATTGACAGTC CAGCT         [SEQ ID No. 172]
Maximum fragment size: 805 nt
Pathogen Name: erm Erythormycin Resistance Genes (in *S. aureus*,
*E. coli*, or *Bacillus sphaericus*)
Gene: erm
Forward Primer: E1
GARATIGGII IIGGIAARGG ICA*                    [SEQ ID No. 173]
Reverse Primer: E2
AAYTGRTTYT TIGTRAA*                           [SEQ ID No. 174]
Maximum fragment size: 530 nt
*I = inosine
Pathogen Name: Methicillin-Resistant Staphylococcus
Gene: mecA
Forward Primer: RSM 2647
AAAATCGATG GTAAAGGTTG GC                      [SEQ ID No. 175]
Site of Specific Hybridization: nt 1282–1303
Reverse Primer: RSM 2648
AGTTCTGCAG TACCGGATTT GC                      [SEQ ID No. 176]
Site of Specific Hybridization: nt 1814–1793
Maximum fragment size: 533 nt
Pathogen Name: Penicillinase-Producing *Neisseria gonorrhoeae*
Gene: TEM-1
Forward Primer: PPNG-L
AGTTATCTAC ACGACGG                            [SEQ ID No. 177]
Reverse Primer: PPNG-R
GGCGTACTAT TCACTCT                            [SEQ ID No. 178]
Maximum fragment size: 761 nt
Pathogen Name: Aminoglycoside-Modifying Enzymes
Gene: aacC1
Forward Primer: aacC1-1
ACCTACTCCC AACATCAGCC                         [SEQ ID No. 179]
Reverse Primer: aacC1-2
ATATAGATCT CACTACGCGC                         [SEQ ID No. 180]
Maximum fragment size: 169 nt
Pathogen Name: Extended Spectrum of Beta-lactamases
Gene: TEM-1
Forward Primer: Lag. Std. 3
AGAGAATTAT GCAGTGC                            [SEQ ID No. 181]
Site of Specific Hybridization: nt 560
Reverse Primer: Amp. Primer 2
GACAGTTACC AATGCTTAAT CA                      [SEQ ID No. 182]
Site of Specific Hybridization: nt 1074
Maximum fragment size: 514 nt
Pathogen Name: Fluoroquinolone Resistance mutations in
*Mycobacterium tuberculosis*
Gene: gyrA
Forward Primer: GyrA1
CAGCTACATC GACTATGCGA                         [SEQ ID No. 183]
Site of Specific Hybridization: nt 78–97
Reverse Primer: GyrA2
GGGCTTCGGT GTACCTCAT                          [SEQ ID No. 184]
Site of Specific Hybridization: nt 379–397
Maximum fragment size: 320 nt

APPENDIX I-continued

Suitable Sequencing Primer Pairs for Identification and
Sub-Typing of Infectious Pathogens
cf. Diagnostic Molecular Microbiology (Eds. Persing et al.)
(1993; American Society for Microbiology; Washington D.C.)

Pathogen Name: Isoniazid Resitance of *Mycobacterium tuberculosis*
Gene: katG
Forward Primer: katG904
AGCTCGTATG GCACCGGAAC                    [SEQ ID No. 185]
Site of Specific Hybridization: nt 904
Reverse Primer: katG1523
TTGACCTCCC ACCCGACTTG                    [SEQ ID No. 186]
Site of Specific Hybridization: nt 1523
Maximum fragment size: 620 nt
Pathogen Name: Vancomycin resistant Enterococci
Gene: vanB
Forward Primer: VanB1
CATCGCCGTC CCCGAATTTC AAA                [SEQ ID No. 187]
Reverse Primer: VanB2
GATGCGGAAG ATACCGTGGC T                  [SEQ ID No. 188]
Maximum fragment size: 297 nt

APPENDIX II

|  |  | 10 | 20 | 30 | 40 | 50 |  |
|---|---|---|---|---|---|---|---|
| OMP-A-1 | 1 | -A----A--- | ------A--A | --A---A--- | A--A-----A | -AAAA--A-- | 50 |
| OMP-A-3 | 1 | -A----A--- | ------A--A | --A-A-A--- | A--A-----A | -AAAA--A-- | 50 |
| OMP-B-1 | 1 | AA-------- | AA----A-AA | --A--A-A-- | -AA------A | -----A---A | 50 |
| OMP-B-2 | 1 | AA-------- | AA----A-AA | --A--A-A-- | -AA------A | -----A---A | 50 |
| OMP-Ba-1 | 1 | AA-------- | AA----A-AA | --A--A-A-- | -AA------A | -----A---A | 50 |
| OMP-C | 1 | -A----A--- | ------A--A | --A---A--- | A--A-----A | -AAAA--A-- | 50 |
| OMP-D-1 | 1 | -A-------- | AA----A-AA | ---A-A-A-- | -AA-A----A | -----A---A | 50 |
| OMP-D-2 | 1 | -A-------- | AA----A-AA | ---A-A-A-- | -AA-A----A | -----A---A | 50 |
| OMP-Da | 1 | -A-------- | AA----A-AA | ---A-A-A-- | -AA-A----A | -----A---A | 50 |
| OMP-E | 1 | AA------A- | AA----A-AA | --A--A-A-- | -AA----A-A | -----AA--A | 50 |
| OMP-H | 1 | -A----A--- | ------A--A | --AA--A--- | A--A-A---A | -AAAA--A-- | 50 |
| OMP-I | 1 | -A----A--- | ------A--A | --AA--A-A- | A--A-----A | -AAAA--A-- | 50 |
| OMP-J | 1 | -A----A--- | ------A--- | --A---A--- | A--A-----A | -AAAA--A-- | 50 |
| OMP-K | 1 | -A----A--- | ------A--A | --A---A--- | A-AA-----A | -AAAA--A-- | 50 |
| OMP-L1 | 1 | AA-------- | AA----A-A- | --A--A-A-- | -AA------A | -----A---A | 50 |
| OMP-L2-1 | 1 | AA-------- | AA----A-AA | -----A-A-- | -AA------A | -----A---A | 50 |
| OMP-L2-3 | 1 | AA-------- | AA----A-AA | -----A-A-- | -AA------- | -----A---A | 50 |
| OMP-L3 | 1 | AA-------- | -A----A--A | --A---A-A- | A--------A | --AAA--A-- | 50 |
| OMP-LGV | 1 | AA-------- | AA----A-A- | -----A-A-- | -AA------A | -----A---A | 50 |

|  |  | 60 | 70 | 80 | 90 | 100 |  |
|---|---|---|---|---|---|---|---|
| OMP-A-1 | 51 | -A--A--AAA | ---------- | --AAA----- | ---A----AA | A-A-A---AA | 100 |
| OMP-A-3 | 51 | -A--A--AAA | ---------- | --AAA----- | ---A----AA | A-A-A---AA | 100 |
| OMP-B-1 | 51 | -----A-A-- | AA-A-A-AA- | -------A-- | ----A-A-A- | --A--A---- | 100 |
| OMP-B-2 | 51 | -----A-A-- | AA-A-A-AA- | -------A-- | ----A-A-A- | --A--A---- | 100 |
| OMP-Ba-1 | 51 | -----A-A-- | AA-A-A-AA- | -------A-- | ----A-A-A- | --A------- | 100 |
| OMP-C | 51 | -AA-AA-AAA | ---------- | --AAA----- | ---A----AA | A-A-A---AA | 100 |
| OMP-D-1 | 51 | -----A-A-- | AA-A-A-AA- | -------A-- | ----A-A-A- | --A--A---- | 100 |
| OMP-D-2 | 51 | -----A-A-- | AA-A-A-AA- | -------A-- | ----A-A-A- | --A--A---- | 100 |
| OMP-Da | 51 | -----A-A-- | AA-A-A-AA- | -------A-- | ----A-A-A- | --A--A---- | 100 |
| OMP-E | 51 | -----A-A-- | AA-A-A-AA- | -------A-- | ----A-A-A- | --A--A---- | 100 |
| OMP-H | 51 | -AAAAA-AAA | ---------- | --AAA----- | ---A----AA | A-A-A---AA | 100 |
| OMP-I | 51 | -AA-AA-AAA | ---------- | --AAA----- | ---A----AA | A-A-A---AA | 100 |
| OMP-J | 51 | -AA-AA-AAA | -A-------- | --AAA----- | ---A----AA | A-A-A---AA | 100 |
| OMP-K | 51 | -AA-AA-AAA | ---------- | --AAA----- | ---A----AA | A-A-A---AA | 100 |
| OMP-L1 | 51 | -----A-A-- | AA-A-A-AA- | -------A-- | ----A-A-A- | --A--A---- | 100 |
| OMP-L2-1 | 51 | -----A-A-- | AA-A-A-AA- | -------A-- | ----A-A-A- | --A--A---- | 100 |
| OMP-L2-3 | 51 | -----A-A-- | AA-A-A-AA- | -------A-- | ----A-A-A- | --A--A---- | 100 |
| OMP-L3 | 51 | -AA-AA-AAA | ---------- | --AAA----- | ---A----AA | A-A-A---AA | 100 |
| OMP-LGV | 51 | -----A-A-- | AA-A-A-AA- | -------A-- | ----A-A-A- | --A--A---- | 100 |

|  |  | 110 | 120 | 130 | 140 | 150 |  |
|---|---|---|---|---|---|---|---|
| OMP-A-1 | 101 | -A-----AAA | -----A--AA | --------A- | A----A--AA | A-A------A | 150 |
| OMP-A-3 | 101 | -A-----AAA | -----A--AA | --------A- | A----A--AA | A-A------A | 150 |
| OMP-B-1 | 101 | -A-A-----A | -AAA------ | ----A----A | ---AA-A--- | ---A------ | 150 |
| OMP-B-2 | 101 | -A-A-----A | -AAA------ | ----A----A | ---AA-A--- | ---A------ | 150 |
| OMP-Ba-1 | 101 | -A-A-----A | -AAA------ | ----A----A | ---AA-A--- | ---A------ | 150 |
| OMP-C | 101 | -A-----AAA | -----A--AA | --------A- | A----A--AA | A-A------A | 150 |

APPENDIX II-continued

| OMP-D-1 | 101 | -A-A-----A | -AAA------ | ----A----A | ---AA-A--- | ---A------ | 150 |
| OMP-D-2 | 101 | -A-A-----A | -AAA------ | ----A----A | ---AA-A--- | ---A------ | 150 |
| OMP-Da  | 101 | -A-A-----A | -AAA------ | ----A----A | ---AA-A--- | ---A------ | 150 |
| OMP-E   | 101 | -A-A-----A | -AAA------ | ----A----A | ---AA-A--- | ---A------ | 150 |
| OMP-H   | 101 | -A-----AAA | -----A--AA | --------A- | A----A--AA | A-A------A | 150 |
| OMP-I   | 101 | -A-----AAA | -----A--AA | --------A- | A----A--AA | A-A------A | 150 |
| OMP-J   | 101 | -A-----AAA | -----A--AA | --------A- | A----A--AA | A-A------A | 150 |
| OMP-K   | 101 | -A-----AAA | -----A--AA | --------A- | A----A--AA | A-A------A | 150 |

We claim:

1. A method for evaluating a natural abundance sample for the presence of a target DNA sequence from a target microorganism, said natural abundance sample containing the target DNA sequence substantially without preferential amplification of the target DNA sequence relative to non-target DNA sequences in the sample, comprising the steps of:

(a) combining the natural abundance sample directly and in a single reaction mixture with first and second primers, a nucleotide triphosphate feedstock mixture, a chain-terminating nucleotide triphosphate and a thermally stable polymerase enzyme which incorporates dideoxynucleotides into an extending nucleic acid polymer at a rate which is no less than 0.4 times the rate of incorporation of deoxynucleotides in an amplification mixture, said first and second primers binding to the sense and antisense strands, respectively, and flanking the target DNA sequence within the target microorganism genome, and at least one of said first and second primers being labeled with a fluorescent label;

(b) exposing the reaction mixture to a plurality of temperature cycles each of which includes at least a high temperature denaturation phase and a lower temperature extension phase, thereby producing a plurality of species of terminated fragments if DNA from the target microorganism is present in the natural abundance sample, each species of terminated fragment corresponding to a different incorporation position for the chain-terminating nucleotide triphosphate in the DNA of the target microorganism DNA;

(c) evaluating the terminated fragments produced to determine the incorporation positions of the chain-terminating nucleotide triphosphate; and (d) comparing the incorporation positions of the chain-terminating nucleotide triphosphate to the target DNA sequence to determine if the target DNA sequence is present in the sample.

2. The method of claim 1, wherein the first and second primers are each labeled with a different fluorescent label.

3. The method of claim 1, wherein the chain terminating nucleotide triphosphate is present in a mole ratio to the corresponding nucleotide triphosphate of from 1:50 to 1:1000.

4. The method of claim 3, wherein the mole ratio of the chain terminating nucleotide triphosphate to the corresponding nucleotide triphosphate is from 1:100 to 1:500.

5. The method according to claim 1, wherein the target microorganism is *Chlamydia trachomatis*.

6. The method according to claim 5, wherein the first and second primers are selected from among the group consisting of the oligonucleotides given by Seq. ID. Nos. 1–17.

7. The method according to claim 1, wherein the target microorganism is human immunodeficiency virus.

8. The method according to claim 7, wherein the first and second primers are selected from among the group consisting of the oligonucleotides given by Seq. ID. Nos. 18–20.

9. The method according to claim 1, wherein the target microorganism is human papilloma virus.

10. The method according to claim 9, wherein the first and second primers are selected from among the group consisting of the oligonucleotides given by Seq. ID. Nos. 21–22.

11. A method for evaluating a natural abundance sample for the presence of a target DNA sequence from a target microorganism, said natural abundance sample containing the target DNA sequence substantially without preferential amplification of the target DNA sequence relative to non-target DNA sequences in the sample, comprising the steps of:

(a) combining each of from one to three aliquots of the natural abundance sample directly and in a single reaction mixture with first and second primers, a nucleotide triphosphate feedstock mixture, a single chain-terminating nucleotide triphosphate and a thermally stable polymerase enzyme which incorporates dideoxynucleotides into an extending nucleic acid polymer at a rate which is no less than 0.4 times the rate of incorporation of deoxynucleotides in an amplification mixture to form a reaction mixture, said first and second primers binding to the sense and antisense strands, respectively, and flanking the target DNA sequence within the target microorganism genome, and at least one of said first and second primers being labeled with a fluorescent label, wherein the chain-terminating nucleotide triphosphate added to each aliquot is different from that added to the other aliquots;

(b) exposing the reaction mixture to a plurality of temperature cycles each of which includes at least a high temperature denaturation phase and a lower temperature extension phase, thereby producing a plurality of species of terminated fragments if DNA from the target microorganism is present in the natural abundance sample, each species of terminated fragment corresponding to a different incorporation position for the chain-terminating nucleotide triphosphate in the DNA of the target microorganism DNA;

(c) evaluating the terminated fragments produced to determine the incorporation positions of the chain-terminating nucleotide triphosphate; and (d) comparing the incorporation positions of the chain-terminating nucleotide triphosphate to the target DNA sequence to determine if the target DNA sequence is present in the sample.

* * * * *